United States Patent
Hassett

(10) Patent No.: US 9,925,206 B2
(45) Date of Patent: Mar. 27, 2018

(54) COMPOSITIONS AND METHODS FOR TREATING BACTERIAL INFECTION

(71) Applicant: University of Cincinnati, Cincinnati, OH (US)

(72) Inventor: Daniel J. Hassett, Cincinnati, OH (US)

(73) Assignee: UNIVERSITY OF CINCINNATI, Cincinatti, OH (US)

( * ) Notice: Subject to any disclaimer, the term of this patent is extended or adjusted under 35 U.S.C. 154(b) by 0 days.

(21) Appl. No.: 15/066,557

(22) Filed: Mar. 10, 2016

(65) Prior Publication Data

US 2016/0263151 A1    Sep. 15, 2016

Related U.S. Application Data

(60) Provisional application No. 62/131,422, filed on Mar. 11, 2015.

(51) Int. Cl.
| | |
|---|---|
| *A61K 31/7036* | (2006.01) |
| *A61K 31/198* | (2006.01) |
| *A61K 33/00* | (2006.01) |

(52) U.S. Cl.
CPC ........ *A61K 31/7036* (2013.01); *A61K 31/198* (2013.01); *A61K 33/00* (2013.01)

(58) Field of Classification Search
CPC .... A61K 31/7036; A61K 31/98; A61K 33/00; A61K 2300/00
See application file for complete search history.

(56) References Cited

U.S. PATENT DOCUMENTS

| | | | |
|---|---|---|---|
| 6,709,681 B2 * | 3/2004 | Benjamin | A01N 59/00 422/29 |
| 2005/0013836 A1 * | 1/2005 | Raad | A61K 45/06 424/400 |
| 2005/0143286 A1 | 6/2005 | Singh et al. | |
| 2008/0260865 A1 | 10/2008 | Hassett | |
| 2008/0305050 A1 | 12/2008 | Timmins et al. | |
| 2009/0042819 A1 | 2/2009 | Ellis et al. | |
| 2014/0242153 A1 | 8/2014 | Mannino et al. | |

OTHER PUBLICATIONS

International Search Report and Written Opinion from Corresponding PCT Application No. PCT/US2016/021765, dated Jun. 10, 2016 (12 sheets).

* cited by examiner

*Primary Examiner* — Ali Soroush
(74) *Attorney, Agent, or Firm* — King & Spalding LLP

(57) ABSTRACT

Compositions and methods of utilizing the same are provided for treating bacterial infections. The compositions comprise acidified nitrite in combination with an iron chelator and an antibiotic. The compositions of the present invention are effective at treating bacterial infections with minimal to no side effects. Surprisingly, the combination of these three agents has a synergistic effect, which advantageously permits a lower dose of one or more of the active agents (e.g., the antibiotic).

17 Claims, 28 Drawing Sheets

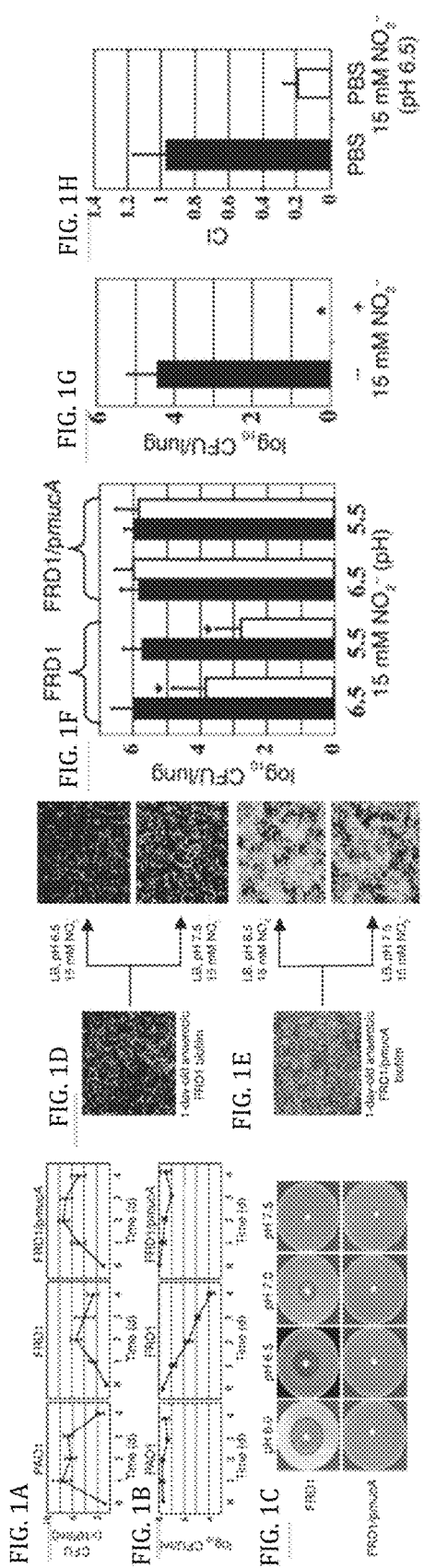

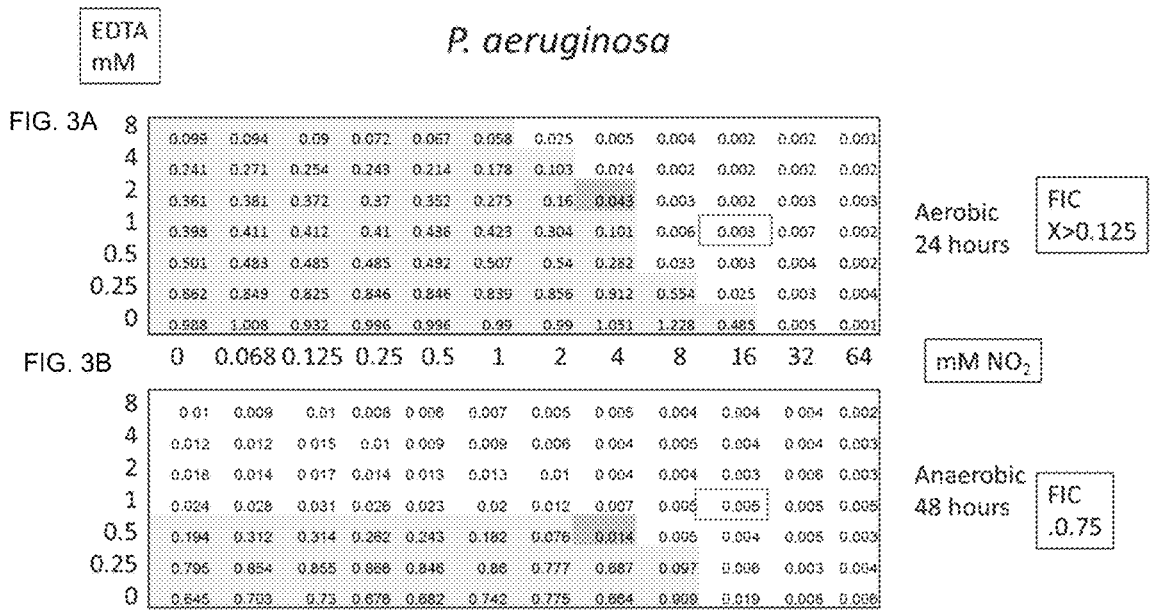

Aerobic
24 hours ug NO₂

Anaerobic
48 hours

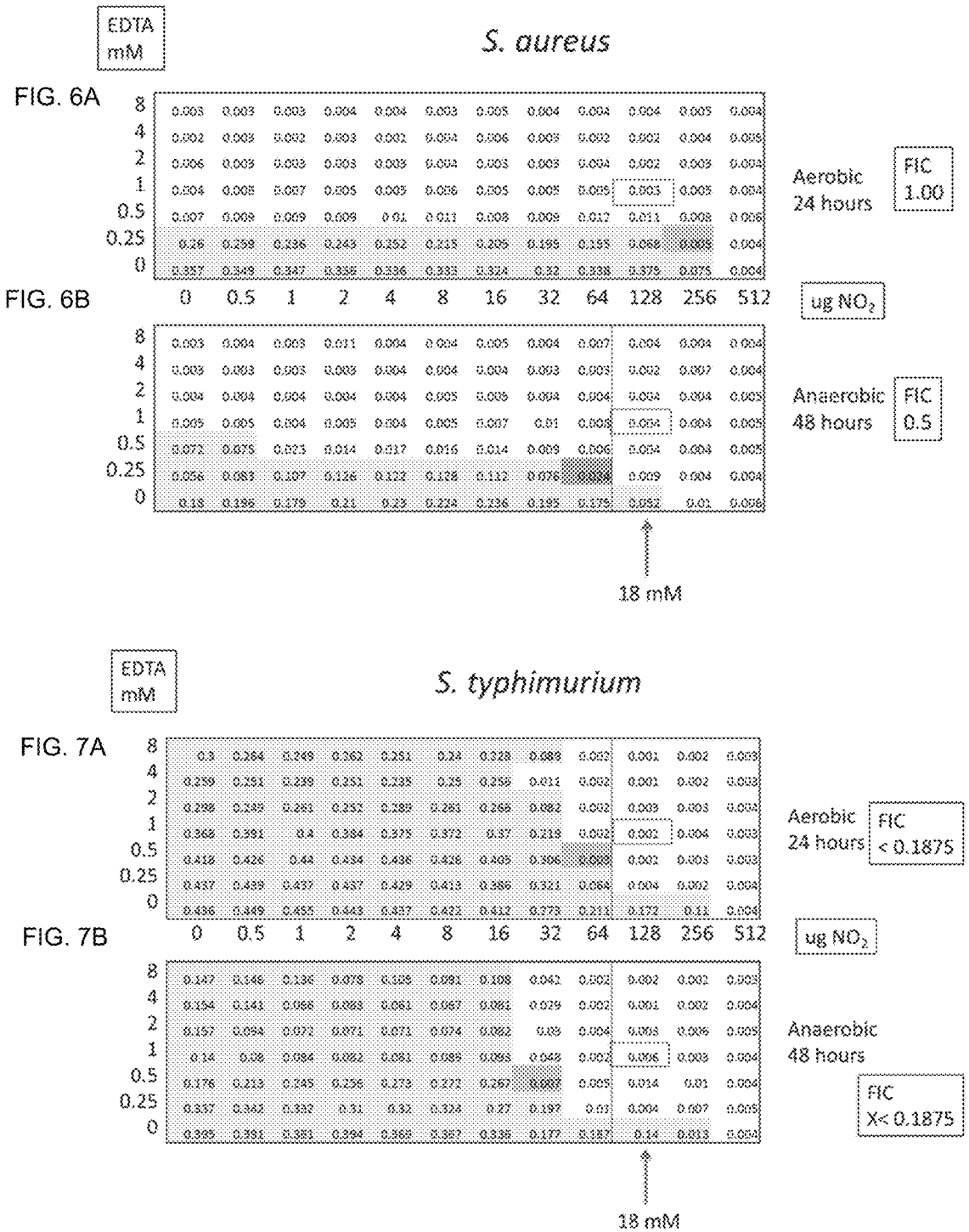

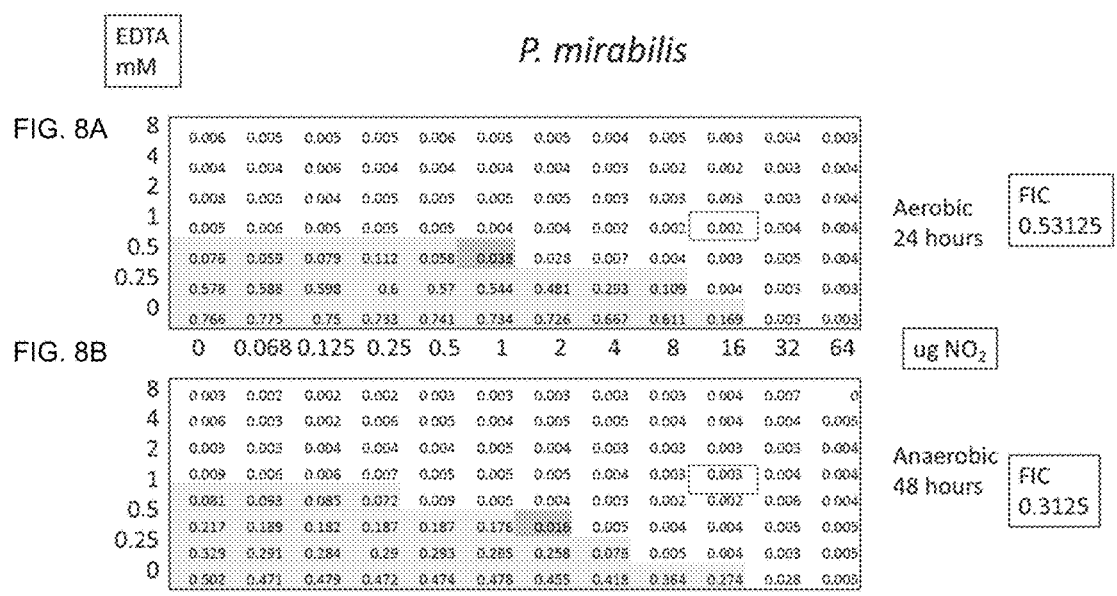
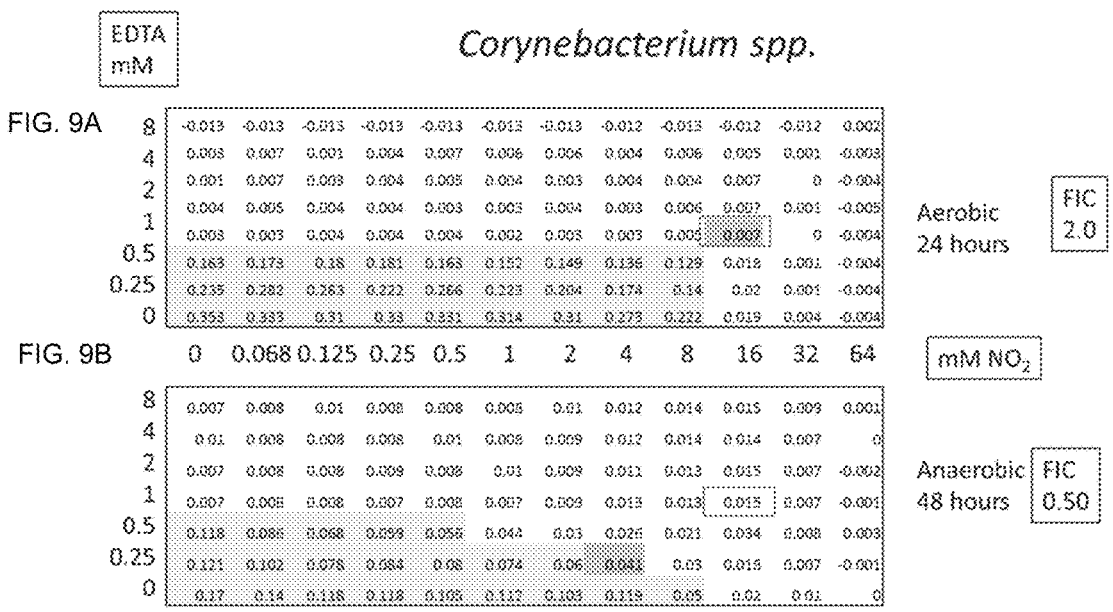

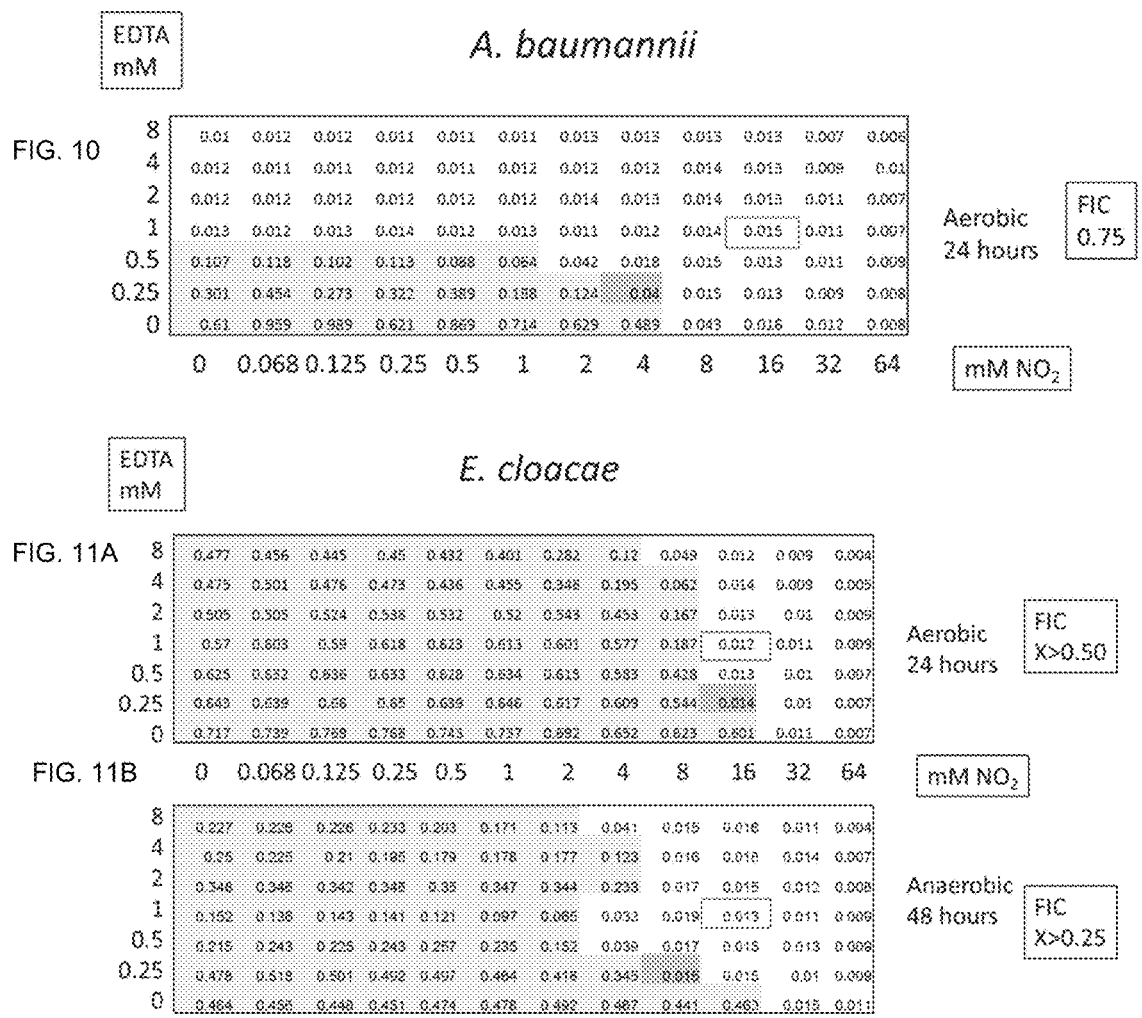

E. faecalis

FIG. 12A

| EDTA mM | 0 | 0.068 | 0.125 | 0.25 | 0.5 | 1 | 2 | 4 | 8 | 16 | 32 | 64 | | |
|---|---|---|---|---|---|---|---|---|---|---|---|---|---|---|
| 8 | 0.003 | 0.003 | 0.003 | 0.003 | 0.007 | 0.004 | 0.009 | 0.008 | 0.003 | 0.003 | 0.002 | 0.001 | | |
| 4 | 0.003 | 0.003 | 0.003 | 0.004 | 0.008 | 0.011 | 0.005 | 0.004 | 0.004 | 0.004 | 0.002 | 0.005 | | |
| 2 | 0.003 | 0.003 | 0.003 | 0.004 | 0.006 | 0.003 | 0.005 | 0.004 | 0.005 | 0.005 | 0.004 | 0.002 | Aerobic 24 hours | FIC X>0.50 |
| 1 | 0.004 | 0.004 | 0.007 | 0.006 | 0.006 | 0.005 | 0.005 | 0.013 | 0.005 | 0.005 | 0.003 | 0.001 | | |
| 0.5 | 0.156 | 0.204 | 0.178 | 0.151 | 0.169 | 0.137 | 0.168 | 0.137 | 0.086 | 0.019 | 0.008 | 0.004 | | |
| 0.25 | 0.26 | 0.258 | 0.245 | 0.235 | 0.234 | 0.225 | 0.225 | 0.226 | 0.207 | 0.185 | 0.153 | 0.112 | | |
| 0 | 0.274 | 0.28 | 0.268 | 0.276 | 0.261 | 0.275 | 0.265 | 0.244 | 0.232 | 0.233 | 0.212 | 0.173 | | |

FIG. 12B — mM NO$_2$

| EDTA mM | 0 | 0.068 | 0.125 | 0.25 | 0.5 | 1 | 2 | 4 | 8 | 16 | 32 | 64 | | |
|---|---|---|---|---|---|---|---|---|---|---|---|---|---|---|
| 8 | 0.004 | 0.004 | 0.004 | 0.004 | 0.005 | 0.005 | 0.005 | 0.005 | 0.004 | 0.008 | 0.005 | 0.002 | | |
| 4 | 0.003 | 0.004 | 0.004 | 0.011 | 0.005 | 0.005 | 0.005 | 0.003 | 0.004 | 0.004 | 0.004 | 0.003 | | |
| 2 | 0.006 | 0.003 | 0.005 | 0.014 | 0.006 | 0.008 | 0.005 | 0.005 | 0.005 | 0.004 | 0.004 | 0.004 | Anaerobic 48 hours | FIC X>0.50 |
| 1 | 0.015 | 0.011 | 0.011 | 0.01 | 0.007 | 0.008 | 0.007 | 0.007 | 0.006 | 0.004 | 0.004 | 0.005 | | |
| 0.5 | 0.156 | 0.147 | 0.151 | 0.142 | 0.148 | 0.116 | 0.087 | 0.084 | 0.088 | 0.064 | 0.009 | 0.006 | | |
| 0.25 | 0.371 | 0.318 | 0.398 | 0.282 | 0.253 | 0.22 | 0.228 | 0.181 | 0.15 | 0.118 | 0.096 | 0.029 | | |
| 0 | 0.419 | 0.325 | 0.43 | 0.403 | 0.318 | 0.239 | 0.265 | 0.167 | 0.158 | 0.153 | 0.151 | 0.153 | | |

S. epidermidis

FIG. 13A

| EDTA mM | 0 | 0.068 | 0.125 | 0.25 | 0.5 | 1 | 2 | 4 | 8 | 16 | 32 | 64 | | |
|---|---|---|---|---|---|---|---|---|---|---|---|---|---|---|
| 8 | 0.002 | 0.005 | 0.004 | 0.003 | 0.004 | 0.005 | 0.004 | 0.005 | 0.004 | 0.006 | 0 | -0.005 | | |
| 4 | 0.003 | 0.004 | 0.003 | 0.004 | 0.003 | 0.005 | 0.004 | 0.006 | 0.006 | 0.007 | 0.001 | -0.004 | | |
| 2 | 0.023 | 0.013 | 0.009 | 0.007 | 0.004 | 0.005 | 0.006 | 0.006 | 0.006 | 0.007 | 0 | -0.007 | Aerobic 24 hours | FIC 0.75 |
| 1 | 0.203 | 0.194 | 0.191 | 0.18 | 0.131 | 0.134 | 0.055 | 0.009 | 0.005 | 0.006 | -0.001 | -0.005 | | |
| 0.5 | 0.888 | 0.922 | 0.818 | 0.839 | 0.781 | 0.687 | 0.446 | 0.119 | 0.022 | 0.005 | -0.001 | -0.004 | | |
| 0.25 | 1.187 | 1.195 | 1.272 | 1.276 | 1.271 | 1.254 | 1.08 | 0.585 | 0.094 | 0.007 | 0 | -0.005 | | |
| 0 | 1.328 | 1.282 | 1.319 | 1.302 | 1.321 | 1.331 | 1.293 | 1.086 | 0.497 | 0.009 | 0 | -0.003 | | |

FIG. 13B — mM NO$_2$

| EDTA mM | 0 | 0.068 | 0.125 | 0.25 | 0.5 | 1 | 2 | 4 | 8 | 16 | 32 | 64 | | |
|---|---|---|---|---|---|---|---|---|---|---|---|---|---|---|
| 8 | 0.006 | 0.004 | 0.005 | 0.005 | 0.005 | 0.005 | 0.006 | 0.007 | 0.01 | 0.009 | 0.006 | -0.003 | | |
| 4 | 0.007 | 0.006 | 0.006 | 0.005 | 0.005 | 0.007 | 0.007 | 0.008 | 0.01 | 0.009 | 0.006 | 0.001 | | |
| 2 | 0.009 | 0.016 | 0.007 | 0.006 | 0.006 | 0.006 | 0.009 | 0.01 | 0.009 | 0.011 | 0.006 | 0 | Anaerobic 24 hours | FIC 2.0 |
| 1 | 0.007 | 0.016 | 0.006 | 0.005 | 0.006 | 0.006 | 0.007 | 0.008 | 0.008 | 0.01 | 0.006 | 0 | | |
| 0.5 | 0.024 | 0.026 | 0.02 | 0.021 | 0.013 | 0.014 | 0.012 | 0.013 | 0.011 | 0.01 | 0.008 | -0.001 | | |
| 0.25 | 0.284 | 0.243 | 0.239 | 0.234 | 0.179 | 0.171 | 0.142 | 0.103 | 0.015 | 0.009 | 0.006 | -0.004 | | |
| 0 | 0.337 | 0.342 | 0.368 | 0.345 | 0.362 | 0.396 | 0.21 | 0.078 | 0.04 | 0.014 | 0.009 | 0.002 | | |

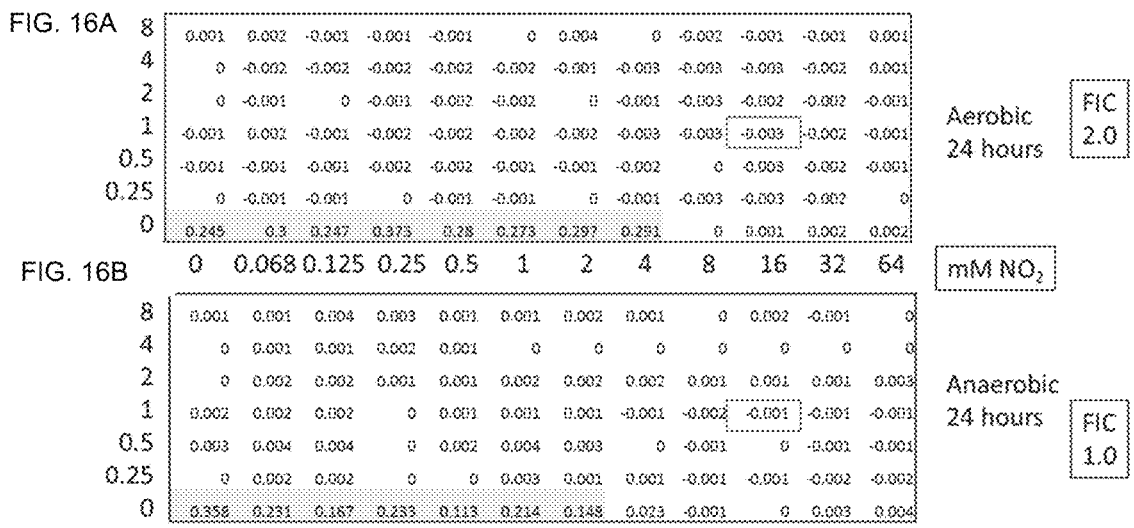
FIG. 16A
FIG. 16B
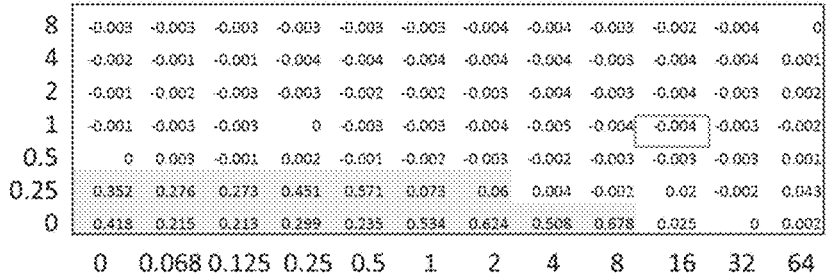
FIG. 17

FIG. 18

Summary of Synergy

| | Gram Negative | | | Gram Positive | |
|---|---|---|---|---|---|
| Bacterium | Aerobic | Anaerobic | Bacterium | Aerobic | Anaerobic |
| P. aeruginosa | Synergy | 0.625 | S. aureus | 1.0 | 0.5 |
| E. coli | Synergy | Synergy | S. epidermidis | 0.75 | 2.0 |
| K. pnuemoniae | Synergy | Synergy | B. anthracis | ND | ND |
| S. maltophila | .625 | N/A | E. faecalis | ~0.5 | ~0.5 |
| A. boumanii | 0.75 | N/A | S. pyogenes | - | - |
| P. mirabilis | .531 | Synergy | L. monocytogenes | 2.0 | 1.0 |
| B. cepacia | 1.0 | N/A | Streptomyces spp. | - | N/A |
| S. typhimurium | Synergy | Synergy | Nocardia sp. | 0.5 | N/A |
| E. cloacae | ~0.5 | Synergy | Corynebacterium | 2.0 | 0.5 |
| H. pylori | - | - | M. smegmatis | - | N/A |

FIG. 19

Concentrations at FIC relevant to current treatment concentrations

| | Aerobic | | Anaerobic | | | Aerobic | | Anaerobic | |
|---|---|---|---|---|---|---|---|---|---|
| Bacterium | NO2 | EDTA | NO2 | EDTA | Bacterium | NO2 | EDTA | NO2 | EDTA |
| P. aeruginosa | ↓ | ↑ | ↓ | ↓ | S. aureus | ↑ | ↓ | ↑ | ↓ |
| E. coli | ↓ | ↓ | ↓ | ↓ | S. epidermidis | ↓ | ↓ | ↓ | ↓ |
| K. pnuemoniae | ↓ | ≈ | ≈ | ↓ | B. anthracis | ND | ND | ND | ND |
| S. maltophila | ↓ | ↓ | N/A | N/A | E. faecalis | ≈ | ↓ | ↑ | ↓ |
| A. baumanii | ↓ | ↓ | N/A | N/A | S. pyogenes | - | - | - | - |
| P. mirabilis | ↓ | ↓ | ↓ | ↓ | L. monocytogenes | ≈ | ↓ | ↓ | ↓ |
| B. cepacia | ↓ | ↓ | N/A | N/A | Streptomyces spp. | - | - | N/A | N/A |
| S. typhimurium | ↓ | ↓ | ↓ | ↓ | Nocardia sp. | ≈ | ↓ | N/A | N/A |
| E. cloacae | ≈ | ↓ | ↓ | ↓ | Corynebacterium | ≈ | ≈ | ↓ | ↓ |
| H. pylori | - | - | - | - | M. smegmatis | - | - | N/A | N/A |

Tobramycin – Aerobic 24 hrs

FIG. 20A

|  |  | 0 | 1/64 | 1/32 | 1/16 | 1/8 | 1/4 | 0.5 | 1 | 2 | 4 | 8 | 16 |  |
|--|--|---|------|------|------|-----|-----|-----|---|---|---|---|----|--|
| | 4 | 0.195 | 0.182 | 0.187 | 0.174 | 0.180 | 0.188 | 0.124 | 0.1 | 0.022 | -0.003 | -0.003 | -0.005 | |
| | 2 | 0.287 | 0.277 | 0.27 | 0.263 | 0.247 | 0.281 | 0.242 | 0.211 | 0.124 | -0.002 | -0.003 | -0.003 | |
| | 1 | 0.359 | 0.366 | 0.357 | 0.346 | 0.372 | 0.33 | 0.342 | 0.301 | 0.246 | 0.073 | -0.002 | -0.004 | No nitrite background |
| mM EDTA | 0.5 | 0.474 | 0.487 | 0.477 | 0.467 | 0.501 | 0.501 | 0.535 | 0.511 | 0.403 | 0.287 | 0.001 | -0.003 | |
| | 0.25 | 0.935 | 0.984 | 0.986 | 0.997 | 0.976 | 0.953 | 0.942 | 0.847 | 0.572 | 0.087 | -0.002 | -0.004 | |
| | 0.125 | 1.101 | 1.103 | 1.084 | 1.123 | 1.091 | 1.087 | 1.118 | 1.063 | 0.879 | -0.002 | -0.004 | -0.004 | |
| | 0 | 1.125 | 1.063 | 1.075 | 1.102 | 1.081 | 1.074 | 1.05 | 0.918 | 0.606 | -0.004 | -0.003 | -0.003 | |

FIG. 20B                0   1/64  1/32  1/16  1/8   1/4   0.5   1    2    4    8    16   ug/mL Toby

|  |  | | | | | | | | | | | | | |
|--|--|--|--|--|--|--|--|--|--|--|--|--|--|
| | 4 | 0.001 | -0.004 | -0.003 | -0.004 | -0.002 | -0.003 | -0.003 | -0.003 | -0.003 | -0.003 | -0.003 | -0.005 | |
| | 2 | -0.003 | -0.004 | -0.003 | -0.004 | -0.003 | -0.003 | -0.004 | -0.004 | -0.003 | -0.001 | -0.003 | -0.004 | FIC 2.0 |
| | 1 | 0.003 | -0.002 | 0 | 0.001 | 0.001 | 0 | -0.002 | -0.003 | -0.003 | -0.003 | -0.002 | -0.004 | |
| mM EDTA | 0.5 | 0.022 | 0.036 | 0.033 | 0.038 | 0.042 | 0.035 | 0.039 | 0.025 | 0.005 | -0.002 | -0.001 | -0.001 | Nitrite (7.5 mM) background |
| | 0.25 | 0.864 | 0.849 | 0.844 | 0.84 | 0.847 | 0.756 | 0.715 | 0.420 | 0.232 | 0.017 | -0.002 | -0.004 | |
| | 0.125 | 1.222 | 1.225 | 1.239 | 1.212 | 1.24 | 1.21 | 1.186 | 1.022 | 0.49 | 0.018 | -0.004 | -0.004 | |
| | 0 | 1.398 | 1.394 | 1.388 | 1.378 | 1.371 | 1.351 | 1.265 | 1.067 | 0.879 | 0.008 | -0.002 | -0.003 | |

Tobramycin – Anaerobic 48 hrs

FIG. 20C

|  |  | | | | | | | | | | | | | |
|--|--|--|--|--|--|--|--|--|--|--|--|--|--|
| | 4 | 0.001 | -0.003 | -0.001 | -0.003 | -0.003 | -0.001 | -0.002 | 0.001 | -0.001 | -0.002 | -0.002 | -0.004 | |
| | 2 | -0.002 | -0.003 | -0.002 | -0.003 | -0.002 | -0.001 | -0.003 | -0.003 | -0.001 | -0.001 | -0.002 | -0.003 | |
| | 1 | 0.008 | 0.001 | 0.002 | 0.002 | 0.001 | 0 | -0.001 | -0.002 | -0.001 | -0.002 | -0.001 | -0.003 | No nitrite background |
| mM EDTA | 0.5 | 0.093 | 0.116 | 0.076 | 0.056 | 0.081 | 0.054 | 0.045 | 0.024 | 0.015 | 0.012 | 0.012 | 0.013 | |
| | 0.25 | 0.27 | 0.29 | 0.307 | 0.23 | 0.268 | 0.218 | 0.238 | 0.18 | 0.123 | 0.022 | 0.015 | 0.011 | |
| | 0.125 | 0.508 | 0.491 | 0.468 | 0.468 | 0.481 | 0.461 | 0.435 | 0.327 | 0.118 | 0.035 | 0.031 | 0.032 | |
| | 0 | 0.604 | 0.522 | 0.617 | 0.515 | 0.603 | 0.518 | 0.581 | 0.395 | 0.118 | 0.038 | 0.036 | 0.037 | |

FIG. 20D                0   1/64  1/32  1/16  1/8   1/4   0.5   1    2    4    8    16   ug/mL Toby

|  | | | | | | | | | | | | | |
|--|--|--|--|--|--|--|--|--|--|--|--|--|--|
| | -0.002 | -0.003 | -0.003 | -0.002 | -0.003 | -0.002 | -0.001 | -0.002 | -0.002 | -0.002 | -0.002 | -0.003 | |
| | -0.003 | -0.001 | -0.003 | -0.003 | -0.003 | -0.002 | -0.003 | -0.003 | -0.002 | -0.002 | -0.002 | -0.003 | |
| | 0.001 | -0.004 | -0.002 | -0.002 | -0.002 | -0.002 | -0.003 | -0.003 | -0.003 | -0.002 | -0.002 | -0.003 | |
| mM EDTA | -0.002 | 0.001 | -0.001 | 0 | -0.002 | -0.002 | -0.001 | -0.002 | -0.001 | -0.001 | 0 | 0 | Nitrite (7.5 mM) background |
| | 0.003 | 0.003 | 0.002 | 0.001 | 0.005 | 0 | 0 | 0.002 | 0 | -0.001 | 0.001 | 0.002 | |
| | 0.235 | 0.189 | 0.215 | 0.143 | 0.095 | 0.086 | 0.085 | 0.063 | 0.02 | 0.005 | 0.005 | 0.006 | |
| | 0.396 | 0.374 | 0.34 | 0.357 | 0.349 | 0.315 | 0.307 | 0.282 | 0.106 | 0.007 | 0.007 | 0.008 | |

Ciprofloxacin – Aerobic 24 hrs

FIG. 21A

| mM EDTA | 0 | 1.95 | 3.9 | 7.8 | 15.7 | 31.3 | 62.5 | 125 | 250 | 500 | 1000 | 2000 |
|---|---|---|---|---|---|---|---|---|---|---|---|---|
| 4 | 0.003 | 0.002 | 0.001 | 0.002 | 0.002 | 0.001 | 0.003 | 0.002 | 0.002 | 0.001 | 0 | 0 |
| 2 | 0.044 | 0.05 | 0.058 | 0.054 | 0.054 | 0.06 | 0.047 | 0.032 | 0.009 | 0.002 | 0.004 | 0.003 |
| 1 | 0.196 | 0.197 | 0.193 | 0.211 | 0.183 | 0.182 | 0.18 | 0.173 | 0.111 | 0.008 | 0.002 | 0 |
| 0.5 | 0.447 | 0.459 | 0.454 | 0.463 | 0.456 | 0.479 | 0.444 | 0.452 | 0.407 | 0.299 | 0.104 | 0.016 |
| 0.25 | 0.682 | 0.722 | 0.74 | 0.724 | 0.725 | 0.738 | 0.713 | 0.685 | 0.59 | 0.464 | 0.368 | 0.035 |
| 0.125 | 0.789 | 0.794 | 0.784 | 0.778 | 0.791 | 0.796 | 0.782 | 0.784 | 0.701 | 0.539 | 0.142 | 0.001 |
| 0 | 0.781 | 0.787 | 0.809 | 0.81 | 0.799 | 0.818 | 0.809 | 0.785 | 0.727 | 0.631 | 0.127 | 0.003 |

FIC 0.75
No nitrite background ng/mL Cipro

FIG. 21B

| mM EDTA | | | | | | | | | | | | | |
|---|---|---|---|---|---|---|---|---|---|---|---|---|
| | 0.001 | 0.002 | 0.001 | 0.002 | 0.001 | 0.003 | 0.001 | 0.001 | 0.001 | 0 | 0.001 | 0 |
| | 0.001 | 0.002 | 0.001 | 0.001 | 0.001 | 0.001 | 0 | 0.001 | 0.001 | 0 | 0.001 | 0.001 |
| | 0.003 | 0.001 | 0 | 0.001 | 0.001 | 0.001 | 0.001 | 0 | 0 | 0 | 0.001 | 0.001 |
| | 0.019 | 0.017 | 0.021 | 0.02 | 0.02 | 0.023 | 0.017 | 0.013 | 0.041 | 0.001 | 0.008 | 0.001 |
| | 0.672 | 0.717 | 0.768 | 0.795 | 0.747 | 0.797 | 0.741 | 0.592 | 0.399 | 0.187 | 0.004 | 0.001 |
| | 0.821 | 0.838 | 0.825 | 0.823 | 0.811 | 0.828 | 0.799 | 0.793 | 0.757 | 0.577 | 0.054 | 0.001 |
| | 0.906 | 0.963 | 0.995 | 0.986 | 0.995 | 0.958 | 0.875 | 0.818 | 0.815 | 0.596 | 0.11 | 0.004 |

FIC 1.0
Nitrite (10 mM) background

Ciprofloxacin – Anaerobic 48 hrs

FIG. 21C

| mM EDTA | | | | | | | | | | | | | |
|---|---|---|---|---|---|---|---|---|---|---|---|---|
| 4 | 0.003 | 0.003 | 0.004 | 0.004 | 0.004 | 0.003 | 0.004 | 0.004 | 0.004 | 0.002 | 0.003 | 0.002 |
| 2 | 0.003 | 0.004 | 0.003 | 0.003 | 0.002 | 0.003 | 0.003 | 0.003 | 0.003 | 0.003 | 0.003 | 0.002 |
| 1 | 0.006 | 0.004 | 0.004 | 0.004 | 0.004 | 0.004 | 0.004 | 0.004 | 0.004 | 0.004 | 0.003 | 0.003 |
| 0.5 | 0.014 | 0.017 | 0.013 | 0.017 | 0.012 | 0.02 | 0.011 | 0.026 | 0.01 | 0.007 | 0.005 | 0.007 |
| 0.25 | 0.16 | 0.145 | 0.149 | 0.161 | 0.167 | 0.166 | 0.155 | 0.145 | 0.126 | 0.093 | 0.052 | 0.013 |
| 0.125 | 0.238 | 0.232 | 0.227 | 0.238 | 0.239 | 0.23 | 0.228 | 0.211 | 0.181 | 0.094 | 0.038 | 0.013 |
| 0 | 0.321 | 0.279 | 0.269 | 0.264 | 0.259 | 0.281 | 0.327 | 0.231 | 0.151 | 0.077 | 0.032 | 0.005 |

No nitrite background ug/mL Toby

FIG. 21D

| mM EDTA | | | | | | | | | | | | | |
|---|---|---|---|---|---|---|---|---|---|---|---|---|
| 4 | 0.003 | 0.004 | 0.003 | 0.003 | 0.003 | 0.003 | 0.004 | 0.003 | 0.003 | 0.002 | 0.002 | 0.003 |
| 2 | 0.003 | 0.003 | 0.003 | 0.003 | 0.003 | 0.003 | 0.003 | 0.002 | 0.003 | 0.003 | 0.003 | 0.003 |
| 1 | 0.006 | 0.003 | 0.003 | 0.003 | 0.003 | 0.003 | 0.003 | 0.002 | 0.003 | 0.002 | 0.003 | 0.003 |
| 0.5 | 0.003 | 0.004 | 0.003 | 0.003 | 0.003 | 0.003 | 0.002 | 0.003 | 0.002 | 0.002 | 0.004 | 0.003 |
| 0.25 | 0.004 | 0.006 | 0.005 | 0.005 | 0.005 | 0.004 | 0.004 | 0.004 | 0.003 | 0.004 | 0.004 | 0.003 |
| 0.125 | 0.053 | 0.058 | 0.048 | 0.059 | 0.043 | 0.039 | 0.041 | 0.038 | 0.033 | 0.012 | 0.006 | 0.006 |
| 0 | 0.231 | 0.212 | 0.231 | 0.196 | 0.212 | 0.235 | 0.228 | 0.21 | 0.184 | 0.143 | 0.028 | 0.003 |

Nitrite (10 mM) background

Ticarcillin – Aerobic 48 hours

FIG. 22A

|  | 0 | 0.5 | 1 | 2 | 4 | 8 | 16 | 32 | 64 | 128 | 256 | 512 |
|---|---|---|---|---|---|---|---|---|---|---|---|---|
| 4 | 0.057 | 0.013 | 0.003 | 0.005 | 0.002 | 0.002 | 0.002 | 0.003 | 0.003 | 0.001 | 0 | 0 |
| 2 | 0.292 | 0.147 | 0.01 | 0.001 | 0.002 | 0.001 | 0.002 | 0.001 | 0.001 | 0.002 | 0.001 | 0.001 |
| 1 | 0.234 | 0.199 | 0.128 | 0.243 | 0.005 | 0.002 | 0.002 | 0.002 | 0.003 | 0.002 | 0.001 | 0.001 |
| 0.5 | 0.488 | 0.483 | 0.384 | 0.365 | 0.199 | 0.438 | 0.001 | 0 | 0 | 0.001 | 0.001 | 0 |
| 0.25 | 0.729 | 0.799 | 0.683 | 0.313 | 0.551 | 0.733 | 0.34 | 0.546 | 0.002 | 0.001 | 0.001 | 0.003 |
| 0.125 | 0.799 | 0.723 | 0.712 | 0.753 | 0.775 | 1.056 | 0.876 | 0.004 | 0.003 | 0.002 | 0.002 | 0.003 |
| 0 | 0.578 | 0.582 | 0.503 | 0.52 | 0.564 | 0.798 | 0.556 | 0.004 | 0.004 | 0.003 | 0.003 | 0.002 | mM EDTA (rows), ug/mL Ticarcillin (columns)

FIC .375 — No nitrite background

FIG. 22B

|  | 0 | 0.5 | 1 | 2 | 4 | 8 | 16 | 32 | 64 | 128 | 256 | 512 |
|---|---|---|---|---|---|---|---|---|---|---|---|---|
| 4 | 0.003 | 0.003 | 0.002 | 0.001 | 0.001 | 0 | 0.002 | 0.001 | 0.001 | 0.001 | 0.001 | 0.003 |
| 2 | 0.046 | 0.026 | 0.004 | 0.001 | 0.001 | 0.001 | 0.001 | 0 | 0.001 | 0.001 | 0.002 | 0.002 |
| 1 | 0.254 | 0.125 | 0.215 | 0.062 | 0.001 | 0.001 | 0.001 | 0.002 | 0.001 | 0.001 | 0.001 | 0.003 |
| 0.5 | 0.395 | 0.371 | 0.32 | 0.198 | 0.005 | 0.005 | 0.003 | 0.002 | 0.002 | 0.002 | 0.002 | 0.001 |
| 0.25 | 0.811 | 0.763 | 0.704 | 0.593 | 0.577 | 0.318 | 0.618 | 0.002 | 0.003 | 0.002 | 0.001 | 0.001 |
| 0.125 | 0.85 | 0.785 | 0.766 | 0.783 | 0.651 | 0.303 | 0.816 | 0.005 | 0.002 | 0.001 | 0.002 | 0.004 |
| 0 | 0.578 | 0.608 | 0.524 | 0.529 | 0.595 | 0.683 | 0.449 | 0.002 | 0.004 | 0.003 | 0.001 | 0.002 |

FIC .375 — Nitrite (3.75 mM) background

Ticarcillin – Anaerobic 48 hours

FIG. 22C

|  | 0 | 0.5 | 1 | 2 | 4 | 8 | 16 | 32 | 64 | 128 | 256 | 512 |
|---|---|---|---|---|---|---|---|---|---|---|---|---|
| 4 | 0.004 | 0.003 | 0.002 | 0.003 | 0.003 | 0.003 | 0.002 | 0.004 | 0.004 | 0.004 | 0.002 | 0.002 |
| 2 | 0.003 | 0.003 | 0.003 | 0.004 | 0.002 | 0.003 | 0.002 | 0.003 | 0.005 | 0.005 | 0.004 | 0.005 |
| 1 | 0.003 | 0.002 | 0.002 | 0.003 | 0.003 | 0.003 | 0.003 | 0.003 | 0.004 | 0.002 | 0.002 | 0.002 |
| 0.5 | 0.05 | 0.032 | 0.017 | 0.011 | 0.006 | 0.003 | 0.003 | 0.002 | 0.003 | 0.002 | 0.003 | 0.003 |
| 0.25 | 0.212 | 0.18 | 0.044 | 0.017 | 0.011 | 0.007 | 0.004 | 0.003 | 0.003 | 0.003 | 0.003 | 0.002 |
| 0.125 | 0.27 | 0.262 | 0.077 | 0.087 | 0.025 | 0.034 | 0.005 | 0.008 | 0.004 | 0.002 | 0.002 | 0.003 |
| 0 | 0.451 | 0.287 | 0.225 | 0.113 | 0.056 | 0.009 | 0.007 | 0.011 | 0.007 | 0.006 | 0.004 | 0.004 |

FIC .375 — No nitrite background

FIG. 22D

|  | 0 | 0.5 | 1 | 2 | 4 | 8 | 16 | 32 | 64 | 128 | 256 | 512 |
|---|---|---|---|---|---|---|---|---|---|---|---|---|
| 4 | 0.004 | 0.004 | 0.004 | 0.004 | 0.004 | 0.005 | 0.004 | 0.004 | 0.004 | 0.004 | 0.004 | 0.003 |
| 2 | 0.004 | 0.005 | 0.004 | 0.003 | 0.004 | 0.005 | 0.003 | 0.003 | 0.003 | 0.003 | 0.006 | 0.003 |
| 1 | 0.004 | 0.007 | 0.004 | 0.004 | 0.004 | 0.005 | 0.004 | 0.005 | 0.007 | 0.004 | 0.01 | 0.005 |
| 0.5 | 0.004 | 0.007 | 0.004 | 0.005 | 0.005 | 0.004 | 0.004 | 0.004 | 0.003 | 0.004 | 0.003 | 0.003 |
| 0.25 | 0.151 | 0.159 | 0.139 | 0.065 | 0.008 | 0.011 | 0.006 | 0.005 | 0.004 | 0.004 | 0.004 | 0.004 |
| 0.125 | 0.349 | 0.359 | 0.353 | 0.205 | 0.087 | 0.022 | 0.013 | 0.011 | 0.005 | 0.004 | 0.004 | 0.003 |
| 0 | 0.487 | 0.354 | 0.275 | 0.242 | 0.11 | 0.045 | 0.011 | 0.009 | 0.008 | 0.007 | 0.006 | 0.003 |

FIC 1.0 — Nitrite (3.75 mM) background

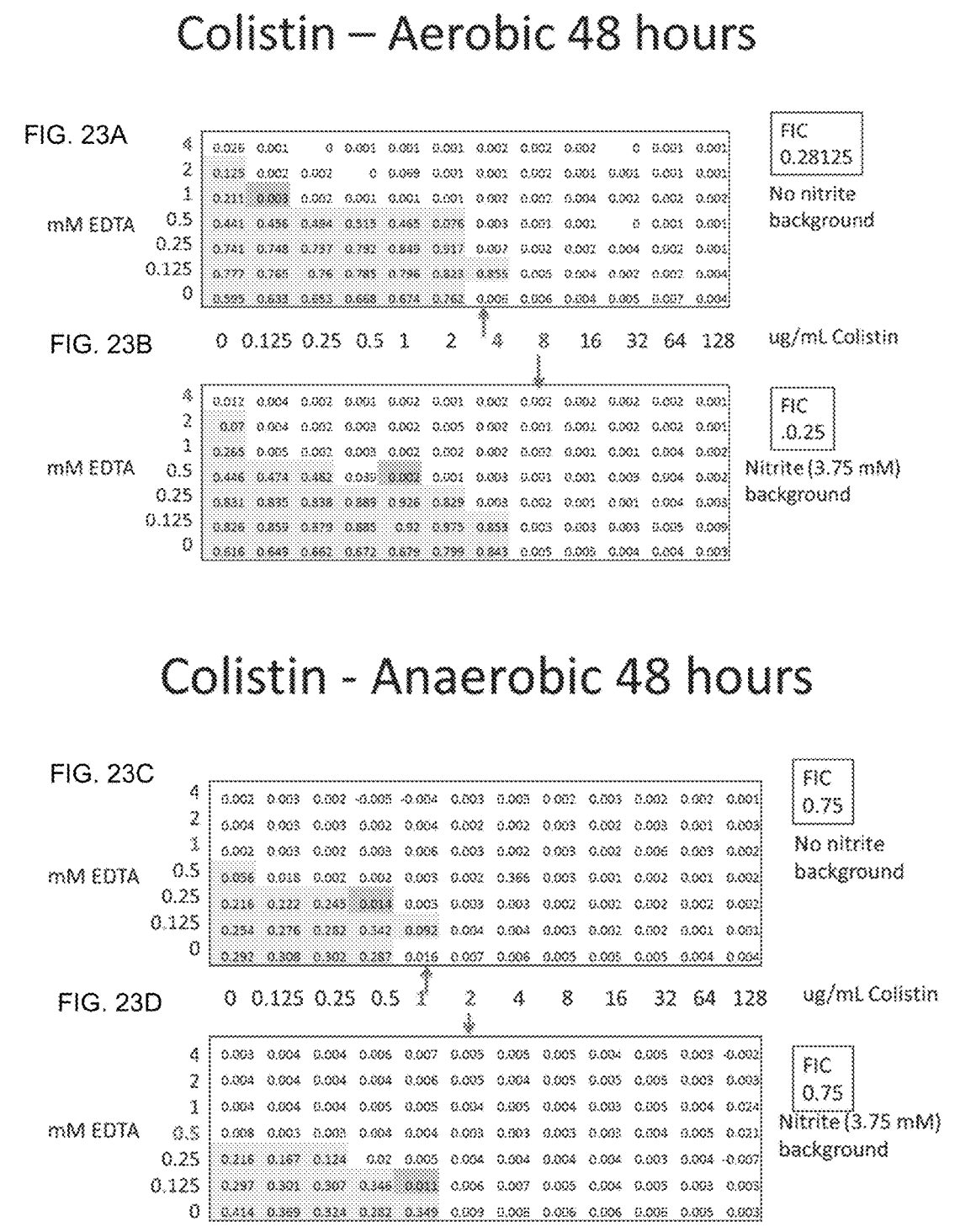

Colistin – Aerobic 48 hours

FIG. 23A

FIC 0.28125
No nitrite background

FIG. 23B 0  0.125  0.25  0.5  1  2  4  8  16  32  64  128   ug/mL Colistin

FIC 0.25
Nitrite (3.75 mM) background

Colistin - Anaerobic 48 hours

FIG. 23C

FIC 0.75
No nitrite background

FIG. 23D 0  0.125  0.25  0.5  1  2  4  8  16  32  64  128   ug/mL Colistin

FIC 0.75
Nitrite (3.75 mM) background

Azithromycin – Aerobic 24 hours

FIG. 24A

|  | 0 | 0.25 | 0.5 | 1 | 2 | 4 | 8 | 16 | 32 | 64 | 128 | 256 |
|---|---|---|---|---|---|---|---|---|---|---|---|---|
| 4 | 0.122 | 0.11 | 0.107 | 0.101 | 0.07 | 0.029 | 0.002 | 0.002 | 0.001 | 0.001 | 0.001 | 0.001 |
| 2 | 0.23 | 0.227 | 0.233 | 0.209 | 0.19 | 0.147 | 0.089 | 0.019 | 0.001 | 0.001 | 0.001 | 0.002 |
| 1 | 0.372 | 0.381 | 0.389 | 0.333 | 0.307 | 0.241 | 0.207 | 0.135 | 0.077 | 0.03 | 0.002 | 0.001 |
| 0.5 | 0.481 | 0.504 | 0.5 | 0.471 | 0.436 | 0.39 | 0.356 | 0.29 | 0.21 | 0.169 | 0.096 | 0.026 |
| 0.25 | 0.871 | 0.865 | 0.858 | 0.853 | 0.808 | 0.73 | 0.675 | 0.608 | 0.509 | 0.397 | 0.286 | 0.176 |
| 0.125 | 1.009 | 0.988 | 1.017 | 0.944 | 0.871 | 0.751 | 0.672 | 0.582 | 0.509 | 0.459 | 0.406 | 0.313 |
| 0 | 1.056 | 1.025 | 0.992 | 0.905 | 0.771 | 0.687 | 0.619 | 0.578 | 0.496 | 0.433 | 0.389 | 0.338 | mM EDTA (rows), ug/mL Azithromycin (columns)

FIC X<0.25 — No nitrite background

FIG. 24B

|  | 0 | 0.25 | 0.5 | 1 | 2 | 4 | 8 | 16 | 32 | 64 | 128 | 256 |
|---|---|---|---|---|---|---|---|---|---|---|---|---|
| 4 | 0.002 | 0.003 | 0.002 | 0.002 | 0.002 | 0.002 | 0.002 | 0.003 | 0.002 | 0.004 | 0.003 | 0.001 |
| 2 | 0.002 | 0.002 | 0.002 | 0.002 | 0.002 | 0.002 | 0.002 | 0.002 | 0.001 | 0.002 | 0.002 | 0.002 |
| 1 | 0.007 | 0.004 | 0.005 | 0.005 | 0.008 | 0.003 | 0.005 | 0.002 | 0.002 | 0.002 | 0.002 | 0.001 |
| 0.5 | 0.04 | 0.038 | 0.045 | 0.04 | 0.037 | 0.024 | 0.017 | 0.004 | 0.002 | 0.002 | 0.002 | 0.001 |
| 0.25 | 0.715 | 0.709 | 0.676 | 0.55 | 0.428 | 0.318 | 0.219 | 0.129 | 0.073 | 0.022 | 0.003 | 0.001 |
| 0.125 | 1.176 | 1.179 | 1.184 | 1.107 | 0.987 | 0.858 | 0.637 | 0.499 | 0.294 | 0.121 | 0.031 | 0.002 |
| 0 | 1.337 | 1.328 | 1.309 | 1.15 | 1.034 | 0.917 | 0.823 | 0.685 | 0.42 | 0.165 | 0.058 | 0.005 |

FIC 0.75 — Nitrite (7.5 mM) background

Azithromycin – Anaerobic 48 hours

FIG. 24C

|  | 0 | 0.25 | 0.5 | 1 | 2 | 4 | 8 | 16 | 32 | 64 | 128 | 256 |
|---|---|---|---|---|---|---|---|---|---|---|---|---|
| 4 | 0.003 | 0.005 | 0.003 | 0.003 | 0.002 | 0.002 | 0.002 | 0.001 | 0.002 | 0.001 | 0.001 | 0.002 |
| 2 | 0.003 | 0.004 | 0.003 | 0.003 | 0.002 | 0.002 | 0.002 | 0.001 | 0.002 | 0.001 | 0.002 | 0.002 |
| 1 | 0.015 | 0.013 | 0.012 | 0.009 | 0.007 | 0.005 | 0.003 | 0.002 | 0.002 | 0.001 | 0.003 | 0.004 |
| 0.5 | 0.138 | 0.134 | 0.13 | 0.12 | 0.113 | 0.072 | 0.034 | 0.008 | 0.003 | 0.002 | 0.004 | 0.002 |
| 0.25 | 0.549 | 0.356 | 0.386 | 0.366 | 0.287 | 0.208 | 0.162 | 0.108 | 0.048 | 0.01 | 0.005 | 0.004 |
| 0.125 | 0.594 | 0.498 | 0.528 | 0.487 | 0.408 | 0.31 | 0.246 | 0.174 | 0.131 | 0.08 | 0.01 | 0.007 |
| 0 | 0.501 | 0.438 | 0.432 | 0.358 | 0.368 | 0.266 | 0.223 | 0.182 | 0.1 | 0.07 | 0.017 | 0.008 |

FIC .0.50 — No nitrite background

FIG. 24D

|  | 0 | 0.25 | 0.5 | 1 | 2 | 4 | 8 | 16 | 32 | 64 | 128 | 256 |
|---|---|---|---|---|---|---|---|---|---|---|---|---|
| 4 | 0.001 | 0.003 | 0.002 | 0.002 | 0.002 | 0.002 | 0.003 | 0.003 | 0.002 | 0.003 | 0.001 | 0 |
| 2 | 0.004 | 0.002 | 0.002 | 0.002 | 0.002 | 0.002 | 0.002 | 0.002 | 0.001 | 0.003 | 0.001 | 0.002 |
| 1 | 0.004 | 0.002 | 0.002 | 0.003 | 0.002 | 0.002 | 0.002 | 0.002 | 0.002 | 0.003 | 0.003 | 0.007 |
| 0.5 | 0.002 | 0.003 | 0.002 | 0.002 | 0.003 | 0.002 | 0.001 | 0.001 | 0.001 | 0.005 | 0.003 | 0.005 |
| 0.25 | 0.036 | 0.026 | 0.011 | 0.005 | 0.004 | 0.003 | 0.002 | 0.002 | 0.003 | 0.003 | 0.002 | 0.002 |
| 0.125 | 0.345 | 0.223 | 0.178 | 0.158 | 0.028 | 0.007 | 0.005 | 0.004 | 0.003 | 0.002 | 0.002 | 0.006 |
| 0 | 0.793 | 0.732 | 0.702 | 0.571 | 0.401 | 0.138 | 0.008 | 0.005 | 0.005 | 0.003 | 0.004 | 0.005 |

FIC 0.75 — Nitrite (7.5 mM) background

Sulfamethazine – Aerobic 48 hours

FIG. 25A

|  mM EDTA | 0 | 0.25 | 0.5 | 1 | 2 | 4 | 8 | 16 | 32 | 64 | 128 | 256 | |
|---|---|---|---|---|---|---|---|---|---|---|---|---|---|
| 4 | | 0.283 | 0.259 | 0.275 | 0.271 | 0.259 | 0.358 | 0.244 | 0.246 | 0.241 | 0.239 | 0.235 | 0.204 |
| 2 | | 0.343 | 0.343 | 0.357 | 0.356 | 0.357 | 0.346 | 0.321 | 0.303 | 0.326 | 0.303 | 0.307 | 0.269 |
| 1 | | 0.484 | 0.478 | 0.483 | 0.477 | 0.48 | 0.462 | 0.439 | 0.461 | 0.443 | 0.474 | 0.448 | 0.386 |
| 0.5 | | 0.88 | 0.875 | 0.898 | 0.702 | 0.72 | 0.713 | 0.551 | 0.596 | 0.588 | 0.687 | 0.7 | 0.668 |
| 0.25 | | 0.983 | 0.993 | 0.98 | 0.973 | 0.983 | 0.938 | 0.939 | 0.983 | 0.878 | 0.973 | 0.862 | 0.918 |
| 0.125 | | 0.984 | 0.941 | 0.988 | 0.975 | 0.96 | 0.968 | 0.629 | 0.891 | 0.873 | 0.982 | 0.944 | 0.986 |
| 0 | | 0.739 | 0.868 | 0.733 | 0.664 | 0.733 | 0.702 | 0.669 | 0.648 | 0.679 | 0.732 | 0.893 | 0.735 |

No nitrite background

FIG. 25B   0   0.25   0.5   1   2   4   8   16   32   64   128   256   ug/mL

| mM EDTA | | | | | | | | | | | | | |
|---|---|---|---|---|---|---|---|---|---|---|---|---|---|
| 4 | | 0 | -0.002 | 0 | -0.003 | -0.002 | 0 | -0.001 | 0 | -0.001 | 0 | 0 | 0 |
| 2 | | 0.004 | 0.005 | 0.005 | 0.027 | 0.007 | 0.004 | -0.001 | 0 | 0.002 | 0.006 | 0.005 | 0.001 |
| 1 | | 0.271 | 0.336 | 0.387 | 0.37 | 0.386 | 0.304 | 0.269 | 0.274 | 0.284 | 0.396 | 0.314 | 0.212 |
| 0.5 | | 0.682 | 0.651 | 0.705 | 0.916 | 0.842 | 0.837 | 0.571 | 0.608 | 0.608 | 0.687 | 0.681 | 0.602 |
| 0.25 | | 1.101 | 1.137 | 1.073 | 1.073 | 1.11 | 1.085 | 1.027 | 1.001 | 1.068 | 1.035 | 1.028 | 1.052 |
| 0.125 | | 1.267 | 1.265 | 1.21 | 1.104 | 1.267 | 1.001 | 1.095 | 1.135 | 1.132 | 1.182 | 1.232 | 1.166 |
| 0 | | 0.86 | 0.831 | 0.808 | 0.798 | 0.796 | 0.779 | 0.787 | 0.793 | 0.8 | 0.852 | 0.873 | 0.939 |

Nitrite (7.5 mM) background

Sulfamethazine – Anaerobic 48 hours

FIG. 25C

| mM EDTA | | | | | | | | | | | | | |
|---|---|---|---|---|---|---|---|---|---|---|---|---|---|
| 4 | | 0.315 | 0.278 | 0.284 | 0.281 | 0.277 | 0.273 | 0.27 | 0.268 | 0.254 | 0.219 | 0.197 | 0.198 |
| 2 | | 0.38 | 0.363 | 0.385 | 0.359 | 0.352 | 0.35 | 0.356 | 0.352 | 0.336 | 0.306 | 0.244 | 0.209 |
| 1 | | 0.468 | 0.479 | 0.474 | 0.464 | 0.46 | 0.444 | 0.432 | 0.425 | 0.438 | 0.402 | 0.309 | 0.188 |
| 0.5 | | 0.664 | 0.632 | 0.656 | 0.616 | 0.605 | 0.588 | 0.581 | 0.563 | 0.564 | 0.638 | 0.612 | 0.534 |
| 0.25 | | 0.928 | 1.027 | 0.988 | 0.974 | 0.995 | 0.878 | 0.958 | 0.949 | 0.911 | 0.898 | 0.862 | 0.898 |
| 0.125 | | 1.02 | 0.968 | 0.968 | 0.979 | 0.973 | 0.967 | 0.891 | 0.934 | 0.947 | 0.898 | 1.013 | 1.113 |
| 0 | | 0.782 | 0.809 | 0.731 | 0.75 | 0.795 | 0.797 | 0.692 | 0.729 | 0.731 | 0.805 | 0.787 | 0.795 |

No nitrite background

FIG. 25D   0   0.25   0.5   1   2   4   8   16   32   64   128   256   ug/mL

| mM EDTA | | | | | | | | | | | | | |
|---|---|---|---|---|---|---|---|---|---|---|---|---|---|
| 4 | | 0 | -0.001 | -0.001 | -0.001 | -0.001 | 0 | 0 | 0 | -0.001 | 0 | 0.003 | -0.001 |
| 2 | | 0.003 | 0.009 | 0.007 | 0.012 | 0.01 | 0.009 | 0.003 | -0.001 | 0.002 | 0.007 | 0.002 | -0.001 |
| 1 | | 0.355 | 0.343 | 0.345 | 0.349 | 0.307 | 0.257 | 0.21 | 0.221 | 0.198 | 0.168 | 0.055 | 0.008 |
| 0.5 | | 0.710 | 0.647 | 0.675 | 0.627 | 0.634 | 0.58 | 0.537 | 0.584 | 0.606 | 0.615 | 0.47 | 0.3 |
| 0.25 | | 1.148 | 0.989 | 1.076 | 1.073 | 1.039 | 1.046 | 1.039 | 1.005 | 1.003 | 0.991 | 0.848 | 0.808 |
| 0.125 | | 1.184 | 1.272 | 1.219 | 1.175 | 1.242 | 1.123 | 1.019 | 1.128 | 1.147 | 1.049 | 1.039 | 1.063 |
| 0 | | 0.993 | 0.961 | 0.792 | 0.741 | 0.768 | 0.793 | 0.782 | 0.753 | 0.864 | 0.837 | 1.173 | 0.849 |

Nitrite (7.5 mM) background

Sulfamethoxazole – Aerobic 48 hours
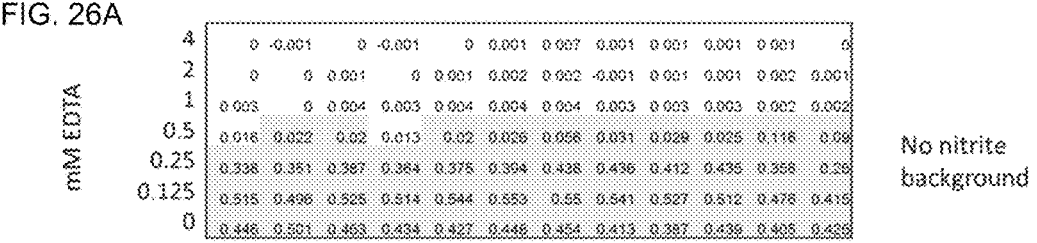
FIG. 26A
FIG. 26B
Sulfamethoxazole – Anaerobic 48 hours
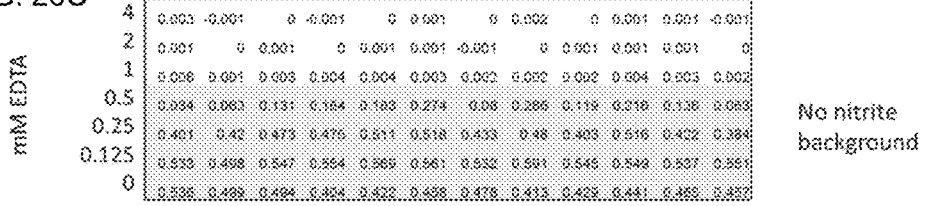
FIG. 26C
FIG. 26D
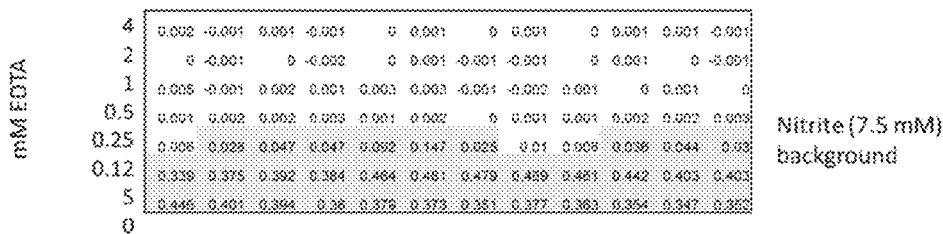

Vancomycin – Aerobic 48 hours

No nitrite background

Nitrite (7.5 mM) background

Vancomycin – Anaerobic 48 hours

No nitrite background

Nitrite (7.5 mM) background

Cefepime – Aerobic 24 hours

No nitrite background

Nitrite (7.5 mM) background

Cefepime – Anaerobic 48 hours

No nitrite background

Nitrite (7.5 mM) background

Imipenem – Aerobic 24 hours

FIG. 29A

|  | 0 | 1/64 | 1/32 | 1/16 | 1/8 | 1/4 | 1/2 | 1 | 2 | 4 | 8 | 16 | ug/mL |
|---|---|---|---|---|---|---|---|---|---|---|---|---|---|
| 4 | 0.003 | 0.035 | 0.043 | 0.032 | 0.027 | 0 | 0 | 0 | 0 | 0 | 0 | -0.002 | |
| 2 | 0.116 | 0.104 | 0.139 | 0.11 | 0.098 | 0.042 | -0.002 | -0.002 | 0.003 | 0 | 0 | -0.001 | |
| 1 | 0.141 | 0.289 | 0.182 | 0.197 | 0.193 | 0.09 | 0.025 | -0.003 | -0.001 | 0 | 0 | -0.001 | No nitrite background |
| 0.5 | 0.477 | 0.419 | 0.483 | 0.529 | 0.329 | 0.313 | 0.429 | 0.043 | 0 | 0.006 | 0 | 0.001 | |
| 0.25 | 0.813 | 1.046 | 0.728 | 0.825 | 0.758 | 0.877 | 1.09 | 0.841 | 0.001 | 0.001 | 0 | -0.001 | |
| 0.125 | 0.764 | 0.816 | 0.786 | 0.881 | 0.811 | 0.754 | 0.616 | 0.727 | 0 | -0.001 | -0.002 | 0 | |
| 0 | 0.543 | 0.481 | 0.876 | 0.387 | 0.474 | 0.473 | 0.432 | 0.448 | 0.01 | -0.002 | 0.001 | 0.001 | | mM EDTA

FIG. 29B   0  1/64  1/32  1/16  1/8  1/4  1/2  1  2  4  8  16   ug/mL

|  |  |  |  |  |  |  |  |  |  |  |  |  |  |
|---|---|---|---|---|---|---|---|---|---|---|---|---|---|
| 4 | 0.003 | -0.001 | 0 | -0.001 | -0.001 | 0.001 | 0.001 | 0.001 | 0.001 | 0.001 | 0.001 | -0.001 | |
| 2 | -0.001 | -0.001 | 0 | -0.001 | 0.001 | 0.011 | 0.06 | 0.03 | 0.002 | 0.001 | 0.001 | -0.001 | |
| 1 | 0.005 | -0.002 | 0.002 | 0.001 | 0 | 0.025 | 0.054 | 0.018 | 0.001 | 0.001 | 0.001 | -0.001 | |
| 0.5 | 0.008 | 0.011 | 0.009 | 0.007 | 0.054 | 0.006 | 0.014 | 0.004 | 0.001 | 0.001 | 0.001 | 0.002 | Nitrite (7.5 mM) background |
| 0.25 | 0.878 | 0.829 | 0.83 | 0.548 | 0.47 | 0.806 | 0.617 | 0.015 | 0.003 | 0.001 | 0.003 | 0 | |
| 0.125 | 0.803 | 0.748 | 1.038 | 0.982 | 0.798 | 0.811 | 0.982 | 0.569 | 0 | 0 | 0.001 | | |
| 0 | 0.549 | 0.807 | 0.445 | 0.514 | 0.448 | 0.814 | 0.598 | 0.568 | 0.001 | -0.001 | 0.002 | 0.003 | | mM EDTA

Imipenem – Anaerobic 48 hours

FIG. 29C

|  |  |  |  |  |  |  |  |  |  |  |  |  |  |
|---|---|---|---|---|---|---|---|---|---|---|---|---|---|
| 4 | 0.001 | -0.001 | -0.001 | -0.002 | -0.002 | 0 | 0.032 | 0.019 | -0.001 | 0.001 | 0 | -0.002 | |
| 2 | -0.002 | -0.002 | -0.001 | -0.001 | 0 | 0.041 | 0.096 | 0.094 | 0.012 | -0.001 | 0 | -0.002 | |
| 1 | 0.004 | -0.002 | 0.001 | 0 | 0.003 | 0.059 | 0.083 | 0.032 | 0.082 | -0.001 | 0 | -0.001 | No nitrite background |
| 0.5 | 0.001 | 0.001 | 0.003 | 0.003 | 0.008 | 0.047 | 0.071 | 0.111 | 0.014 | -0.001 | 0 | 0.001 | |
| 0.25 | 0.066 | 0.105 | 0.062 | 0.08 | 0.097 | 0.06 | 0.046 | 0.019 | 0 | -0.001 | 0 | 0 | |
| 0.125 | 0.182 | 0.13 | 0.127 | 0.122 | 0.135 | 0.108 | 0.03 | 0.004 | -0.003 | -0.001 | -0.001 | -0.001 | |
| 0 | 0.21 | 0.183 | 0.197 | 0.158 | 0.122 | 0.148 | 0.049 | 0.015 | 0.001 | -0.003 | 0.001 | 0.001 | | mM EDTA

FIG. 29D   0  1/64  1/32  1/16  1/8  1/4  1/2  1  2  4  8  16   ug/mL

|  |  |  |  |  |  |  |  |  |  |  |  |  |  |
|---|---|---|---|---|---|---|---|---|---|---|---|---|---|
| 4 | 0.001 | 0 | 0 | 0 | -0.001 | 0 | 0.002 | 0.003 | 0.001 | 0.003 | 0.003 | -0.001 | |
| 2 | -0.001 | -0.001 | 0 | -0.001 | 0 | 0.001 | -0.001 | -0.001 | 0.001 | 0.002 | 0.001 | 0.003 | |
| 1 | 0.003 | -0.003 | 0.001 | 0.001 | 0.001 | 0.001 | 0 | -0.001 | 0.002 | 0.001 | 0.001 | 0.002 | |
| 0.5 | 0.001 | 0.001 | 0.003 | 0.002 | 0.003 | 0.003 | 0.001 | 0.004 | 0.004 | 0.003 | 0.003 | 0.003 | Nitrite (7.5 mM) background |
| 0.25 | 0 | 0.004 | 0.003 | 0.002 | 0.003 | 0.004 | 0.002 | 0.001 | 0.002 | 0.002 | 0.002 | 0.002 | |
| 0.125 | 0.002 | 0.001 | 0.002 | 0.007 | 0.006 | 0.002 | 0.002 | 0 | 0 | 0 | 0.001 | 0.018 | |
| 0 | 0.006 | 0.007 | 0.007 | 0.004 | 0.006 | 0.006 | 0.006 | 0.003 | 0.004 | 0.001 | 0.015 | 0.004 | | mM EDTA

Tetracycline – Aerobic 24 hours

No nitrite background ug/mL

Nitrite (7.5 mM) background

Tetracycline – Anaerobic 48 hours

No nitrite background 0   1/64  1/32  1/16  1/8  1/4  1/2  1  2  4  8  16   ug/mL Nitrite (7.5 mM) background

FIG. 31

Artificial Urine Media and Volunteer Urine Analysis

| | | AUM 5.5 | AUM 6.5 | #1 pH 5.48 | #2 pH 5.74 | #3 pH 5.79 | #4 pH 5.49 | #5 pH 5.50 |
|---|---|---|---|---|---|---|---|---|
| FIC Values (less than 0.5 = synergy) | P. a. | 0.750 | 0.625 | | 0.53 | | 0.500 | |
| | E. c. | 0.625 | 0.5675 | 0.5675 | 0.5675 | 0.5675 | < 0.625 | ~ 0.500 |
| | S. a. | 0.500 | 0.625 | | ND | 0.625 | 0.500 | 0.750 |
| | K. p. | < | < 0.50 | | .750 | 1.00 | < 0.750 | < 1.00 |
| | S. s. | | < | 0.750 | 0.5675 | | 0.625 | 0.750 |
| | | AUM 5.5 | AUM 6.5 | #1 pH 5.48 | #2 pH 5.74 | #3 pH 5.79 | #4 pH 5.49 | #5 pH 5.50 |
| Below Recommended Values? (15 mM $NO_2^-$ and 1 mM EDTA) | P. a. | ✓ | ✗ | ✓ | ✓ | ✓ | ✓ | ✓ |
| | E. c. | ✓ | ✗ | ✓ | ✓ | ✓ | ✓ | ✓ |
| | S. a. | ✓ | ✗ | ✓ | ✓ | ✓ | ✓ | ✓ |
| | K. p. | ✓ | ✗ | ✓ | ✓ | ✓ | ✓ | ✓ |
| | S. s. | ✓ | ✗ | ✓ | ✓ | ✓ | ✓ | ✓ |

US 9,925,206 B2

COMPOSITIONS AND METHODS FOR TREATING BACTERIAL INFECTION

CROSS REFERENCE TO RELATED APPLICATIONS

This application claims the benefit of U.S. provisional patent application 62/131,422 filed Mar. 11, 2015 the content of which are incorporated by reference in their entirety.

FIELD OF THE INVENTION

The present invention relates to compositions and methods of utilizing the same for treating bacterial infections. More specifically, the present invention relates to compositions comprising acidified nitrite in combination with an iron chelator and an antibiotic, as well as methods of utilizing the same for treating bacterial infections.

BACKGROUND OF THE INVENTION

Bacterial infections are commonly associated with many diseases and disorders. Some bacteria form highly organized and uniquely structured communities known as biofilms and it is believed that the structure of biofilms and the altered physiology of biofilm bacteria allows bacteria to resist conventional front-line antibiotics and/or human phagocytes. One such biofilm-forming bacterium is *Pseudomonas aeruginosa*. *Pseudomonas aeruginosa* (PA or *P. aeruginosa*) is a gram-negative bacterium that rarely causes disease in healthy subjects, but is a dominant, opportunistic pathogen adversely affecting patients in diseases such as cystic fibrosis (CF) or chronic obstructive pulmonary disease (COPD). PA is also one of the most common pathogens observed in intensive care units (ICUs) (Jarvis, W. R. et al., 1992, J. Antimicrob. Chemother. 29 (a supp.):19-24). Mortality rates as high as 50% have been reported from PA infections.

Interestingly, there is solid evidence in the literature that at least in CF subjects, some populations of PA are growing either microaerobically (Alvarez-Ortega C, and Harwood C S. 2007 Mol Microbiol 65:153-165.) or anaerobically, in the deepest mucus pockets (Worlitzsch D, et al. 2002. J. Clin. Invest. 109:317-325; Yoon S S, et al. 2002. Dev Cell 3:593-603; Hassett D J, et al. 2002. Adv Drug Deliv Rev 54:1425-1443; Hassett D J, et al. 2004, In, Strict and Facultative Anaerobes: Medical and Environmental Aspects: 87-108).

What is therefore needed are new therapeutic approaches for treating bacterial infections. Of particular importance are *Burkholderia cepacia* and *S. aureus* infections, and more particularly, *P. aeruginosa* infections in patients with CF or COPD, but new therapeutic approaches are needed for other gram negative bacterial infections as well

SUMMARY OF THE INVENTION

The present invention is directed to compositions and methods of utilizing the same for treating bacterial infections wherein the compositions comprise acidified nitrite in combination with an iron chelator and an antibiotic. The compositions of the present invention are effective at treating bacterial infections with minimal to no side effects. Surprisingly, the combination of these three agents has a synergistic effect, which advantageously permits a lower dose of one or more of the active agents (e.g., the antibiotic).

In a first aspect, the invention provides a composition comprising a therapeutically effect amount of acidified nitrite ($A\text{-}NO_2^-$), an iron chelator agent and an antibiotic agent.

In one embodiment, the composition comprises an acidified nitrite ($A\text{-}NO_2^-$), an iron chelator agent (C), and an antibiotic agent (Ab), wherein the $A\text{-}NO_2^-$, C and Ab are provided in a ratio ($A\text{-}NO_2^-$:C:Ab) of about 10-600:1-100: 0.01-6000, about 30-600:1-100:0.01-6000, about 30:1:0.01, about 300:1:0.01, about 600:1:0.01, about 30:10:0.01, about 30:100:0.01, about 30:1:0.1, about 30:1:1, about 30:1:10, about 30:10:100, about 30:10:1000, or about 30:10:6000.

In one embodiment, the therapeutically effective amount of $A\text{-}NO_2^-$ is between about 5 and about 300 mM, between about 5 and about 200 mM, between about 5 and about 100 mM, between about 10 and about 300 mM, between about 10 and about 200 mM, between about 10 and about 100 mM, between about 15 and about 300 mM, between about 15 and about 200 mM, or between about 15 and about 100 mM.

In one embodiment, the therapeutically effective amount of $A\text{-}NO_2^-$ is between about 5 and about 50 mM, between about 5 and about 40 mM, between about 5 and about 30 mM, between about 5 and about 20 mM, or between about 5 and about 10 mM.

In one embodiment, the therapeutically effective amount of $A\text{-}NO_2^-$ is between about 10 and about 50 mM, between about 10 and about 40 mM, between about 10 and about 30 mM, or between about 10 and about 20 mM.

In one embodiment, the therapeutically effective amount of $A\text{-}NO_2^-$ is between about 15 and about 50 mM, between about 15 and about 40 mM, between about 15 and about 30 mM, or between about 15 and about 20 mM.

In one embodiment, the therapeutically effective amount of $A\text{-}NO_2^-$ is about 15 mM for anaerobic growth.

In one embodiment, the therapeutically effective amount of $A\text{-}NO_2^-$ is about 25 mM for aerobic growth.

In various embodiments, the $A\text{-}NO^{2-}$ is administered as a sodium salt, potassium salt, magnesium salt, or calcium salt.

In various embodiments, the $A\text{-}NO^{2-}$ is administered as $NaNO_2$.

In one embodiment, the iron chelator agent is selected from the group consisting of citric acid, phosphates, the di-, tri- and tetra-sodium salts of ethylene diamine tetraacetic acid (EDTA), ethylene glycol-bis-(b-aminoethylether)-N,N, N',N'-tetraacetic acid (EGTA); 1,2-bis(2-aminophenoxy) ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochioride (TRIEN), diethylenetriamin-pentaacetic acid (DPTA), triethylenetetramine hexaacetic acid (TTG), deferoxamine (DFO), deferasirox (DSX), Dimercaprol, zinc citrate, penicilamine succimer, Editronate, sodium hexmetaphosphate and edetate calcium disodium and combinations thereof.

In one embodiment, the iron chelator agent is ethylene diamine tetraacetic acid (EDTA).

In one embodiment, the iron chelator agent is deferoxamine (DFO).

In one embodiment, the iron chelator agent is deferasirox (DSX).

In one embodiment, the iron chelator agent is a di-, tri- or tetra-sodium salt of the iron chelator. In one embodiment, the iron chelator is the di-sodium salt of EDTA.

In one embodiment, the therapeutically effective amount of the iron chelator agent is between about 0.1 and about 50 mM, between about 0.1 and about 30 mM, between about 0.1 and about 10 mM, or between about 0.1 and about 5 mM.

In one embodiment, the therapeutically effective amount of the iron chelator agent is between about 0.5 and about 50 mM, between about 0.5 and about 30 mM, between about 0.5 and about 10 mM, or between about 0.5 and about 5 mM.

In one embodiment, the therapeutically effective amount of the iron chelator agent is between about 1 and about 50 mM, between about 1 and about 30 mM, between about 1 and about 10 mM, or between about 1 and about 5 mM.

In one embodiment, the therapeutically effective amount of the iron chelator agent is between about 5 and about 50 mM, between about 5 and about 30 mM, between about 5 and about 10 mM, or between about 5 and about 5 mM.

In one embodiment, the therapeutically effective amount of the iron chelator agent is about 0.5 mM.

In one embodiment, the antibiotic agent treats a gram negative bacterial infection.

In one embodiment, the antibiotic agent treats a *Pseudomonas* bacterial infection.

In one embodiment, the antibiotic agent treats a *S. aureus* bacterial infection.

In one embodiment, the antibiotic agent is an aminoglycoside antibiotic agent.

In one embodiment, the aminoglycoside antibiotic agent is selected from kanaymycin A, amikacin, arbekacin, bekanamycin, tobramycin, dibekacin, spectinomycin, hygromycin B, verdamicin, astromycin, gentamicin, sisomicin, netilmicin, neomycins B, C, neomycin E (paromomycin), framycetin, ribostamycin, dihydrostreptomycin, or streptomycin.

In one embodiment, the aminoglycoside antibiotic agent is tobramycin.

In one embodiment, the therapeutically effective amount of the antibiotic agent is between about 0.001 mM and about 300 mM, between about 0.001 mM and about 200 mM, between about 0.001 mM and about 100 mM, between about 0.001 mM and about 10 mM, between about 0.001 mM and about 1 mM, between about 0.001 mM and about 0.5 mM, between about 0.001 mM and about 0.1 mM, or between about 0.001 mM and about 0.01 mM.

In one embodiment, the therapeutically effective amount of the antibiotic agent is between about 0.003 mM and about 300 mM, between about 0.003 mM and about 200 mM, between about 0.003 mM and about 100 mM, between about 0.003 mM and about 10 mM, between about 0.003 mM and about 1 mM, between about 0.003 mM and about 0.5 mM, between about 0.003 mM and about 0.1 mM, or between about 0.003 mM and about 0.01 mM.

In one embodiment, the therapeutically effective amount of the antibiotic agent is between about 0.005 mM and about 300 mM, between about 0.005 mM and about 200 mM, between about 0.005 mM and about 100 mM, between about 0.005 mM and about 10 mM, between about 0.005 mM and about 1 mM, between about 0.005 mM and about 0.5 mM, between about 0.005 mM and about 0.1 mM, or between about 0.005 mM and about 0.01 mM.

In one embodiment, the therapeutically effective amount of the antibiotic agent is about 5 µM.

In one embodiment, the therapeutically effective amount of the antibiotic agent is about 4.23 µM.

In one embodiment, the composition further comprises one or more pharmaceutically or physiologically acceptable carriers, diluents or excipients.

The composition may be formulated for any appropriate mode of administration, for example, aerosol, topical, oral, nasal, intravenous, intracranial, intraperitoneal, subcutaneous, intravesicular or intramuscular administration.

In one embodiment, the composition is formulated for administration by inhalation.

In one embodiment, the composition is formulated as a dry powder for administration by inhalation.

In one embodiment, the composition is formulated as a topical gel, cream or paste and the like.

In one embodiment, the composition is formulated as an oral rinse or irrigation solution.

In a second aspect the invention provides a kit comprising individual doses of the composition, applicator tools such as but not limited to wipes or swabs or spray nozzles.

In a third aspect the invention provides methods of treating a bacterial infection or colonization comprising administering to a subject in need thereof a pharmaceutical formulation comprising therapeutically effective amounts of:

A-NO2$^-$;
i. an iron chelator agent; and
ii. an antibiotic agent,
iii. resulting in treatment of the bacterial infection or colonization.

In one embodiment, the bacterial infection is a gram negative bacterial infection.

In one embodiment, the bacterial infection is a *Pseudomonas* infection.

In one embodiment, the bacterial infection is a *S. aureus* infection.

In one embodiment, the composition comprises an acidified nitrite (A-NO2$^-$), an iron chelator agent (C), and an antibiotic agent (Ab), wherein A-NO2$^-$, C and Ab are provided in a ratio (A-NO2$^-$:C:Ab) of about 10-600:1-100:0.01-6000, about 30-600:1-100:0.01-6000, about 30:1:0.01, about 300:1:0.01, about 600:1:0.01, about 30:10:0.01, about 30:100:0.01, about 30:1:0.1, about 30:1:1, about 30:1:10, about 30:10:100, about 30:10:1000, or about 30:10:6000.

In one embodiment, the therapeutically effective amount of A-NO$_2^-$ is between about 5 and about 300 mM, between about 5 and about 200 mM, between about 5 and about 100 mM, between about 10 and about 300 mM, between about 10 and about 200 mM, between about 10 and about 100 mM, between about 15 and about 300 mM, between about 15 and about 200 mM, or between about 15 and about 100 mM.

In one embodiment, the therapeutically effective amount of A-NO$_2^-$ is between about 5 and about 50 mM, between about 5 and about 40 mM, between about 5 and about 30 mM, between about 5 and about 20 mM, or between about 5 and about 10 mM.

In one embodiment, the therapeutically effective amount of A-NO$_2^-$ is between about 10 and about 50 mM, between about 10 and about 40 mM, between about 10 and about 30 mM, or between about 10 and about 20 mM.

In one embodiment, the therapeutically effective amount of A-NO$_2^-$ is between about 15 and about 50 mM, between about 15 and about 40 mM, between about 15 and about 30 mM, or between about 15 and about 20 mM.

In one embodiment, the iron chelator is selected from the group consisting of citric acid, phosphates, the di-, tri- and tetra-sodium salts of ethylene diamine tetraacetic acid (EDTA), ethylene glycol-bis-(b-aminoethylether)-N,N,N', N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochioride (TRIEN), diethylenetriamin-pentaacetic acid (DPTA), triethylenetetramine hexaacetic acid (TTG), deferoxamine (DFO), deferasirox (DSX), Dimercaprol, zinc citrate, penicilamine succimer, Editronate, sodium hexmetaphosphate and edetate calcium disodium and combinations thereof.

In one embodiment, the iron chelator agent is ethylene diamine tetraacetic acid (EDTA).

In one embodiment, the iron chelator agent is deferoxamine (DFO).

In one embodiment, the iron chelator agent is deferasirox (DSX).

In one embodiment, the iron chelator agent is a di-, tri- or tetra-sodium salt of the iron chelator. In one embodiment, the iron chelator agent is the di-sodium salt of EDTA.

In one embodiment, the therapeutically effective amount of the iron chelator agent is between about 0.1 and about 50 mM, between about 0.1 and about 30 mM, between about 0.1 and about 10 mM, or between about 0.1 and about 5 mM.

In one embodiment, the therapeutically effective amount of the iron chelator agent is between about 0.5 and about 50 mM, between about 0.5 and about 30 mM, between about 0.5 and about 10 mM, or between about 0.5 and about 5 mM.

In one embodiment, the therapeutically effective amount of the iron chelator agent is between about 1 and about 50 mM, between about 1 and about 30 mM, between about 1 and about 10 mM, or between about 1 and about 5 mM.

In one embodiment, the therapeutically effective amount of the iron chelator agent is between about 5 and about 50 mM, between about 5 and about 30 mM, between about 5 and about 10 mM, or between about 5 and about 5 mM.

In one embodiment, the therapeutically effective amount of the iron chelator agent is about 0.5 mM.

In one embodiment, the antibiotic agent is selected from aminoglycosides, tetracyclines, sulfonamides, fluoroquinolones, macrolides, oxazolidinones, monobactams, cephalosporins, penicillins, polymyxins, glycylcyclines, and lincosamides.

In one embodiment, the antibiotic agent is an aminoglycoside antibiotic agent.

In one embodiment, the aminoglycoside antibiotic agent is selected from kanaymycin A, amikacin, arbekacin, bekanamycin, tobramycin, dibekacin, spectinomycin, hygromycin B, verdamicin, astromycin, gentamicin, sisomicin, netilmicin, neomycins B, C, neomycin E (paromomycin), framycetin, ribostamycin, dihydrostreptomycin, or streptomycin.

In one embodiment, the aminoglycoside antibiotic agent is tobramycin.

In one embodiment, the therapeutically effective amount of the antibiotic agent is between about 0.001 mM and about 300 mM, between about 0.001 mM and about 200 mM, between about 0.001 mM and about 100 mM, between about 0.001 mM and about 10 mM, between about 0.001 mM and about 1 mM, between about 0.001 mM and about 0.5 mM, between about 0.001 mM and about 0.1 mM, or between about 0.001 mM and about 0.01 mM.

In one embodiment, the therapeutically effective amount of the antibiotic agent is between about 0.003 mM and about 300 mM, between about 0.003 mM and about 200 mM, between about 0.003 mM and about 100 mM, between about 0.003 mM and about 10 mM, between about 0.003 mM and about 1 mM, between about 0.003 mM and about 0.5 mM, between about 0.003 mM and about 0.1 mM, or between about 0.003 mM and about 0.01 mM.

In one embodiment, the therapeutically effective amount of the antibiotic agent is between about 0.005 mM and about 300 mM, between about 0.005 mM and about 200 mM, between about 0.005 mM and about 100 mM, between about 0.005 mM and about 10 mM, between about 0.005 mM and about 1 mM, between about 0.005 mM and about 0.5 mM, between about 0.005 mM and about 0.1 mM, or between about 0.005 mM and about 0.01 mM.

In one embodiment, the therapeutically effective amount of the antibiotic agent is about 5 μM.

In one embodiment, the therapeutically effective amount of the antibiotic agent is about 4.23 μM.

In one embodiment, the bacterial infection is selected from members of genera *Escherichia, Salmonella, Listeria, Campylobacter, Shigella, Brucella, Helicobactor, Mycobacterium, Streptococcus, Staphylococcus*, and *Pseudomonas* infection.

In one embodiment, the bacterial infection is a *P. aeruginosa* infection.

In one embodiment, the *Pseudomonas* infection (e.g., *P. aeruginosa* infection) is a lung infection, an ocular infection, a burn infection, a wound infection, a skin infection, a blood infection, a bone infection, or a combination of two or more of said infections.

In one embodiment, the subject has been diagnosed with CF.

In one embodiment, the subject has been diagnosed with COPD.

In one embodiment, the subject has been diagnosed with ventilator associated pneumonia.

In one embodiment, the subject has been diagnosed with chronic bronchiectasis.

In one embodiment, the subject has been diagnosed with bacterial pneumonia.

In one embodiment, the subject has been diagnosed with pressure ulcers.

In one embodiment, the subject has been diagnosed with diabetic foot ulcers.

In one embodiment, the subject has been diagnosed with bacteremia, upper and lower respiratory tract infections, skin and soft-tissue infections, urinary tract infections (UTIs), endocarditis, intra-abdominal infections, septic arthritis, osteomyelitis, CNS infections, or ophthalmic infections.

In one embodiment, the subject has been diagnosed with CF and only NaNO$_2$ is administered without a diluent. The CF airway pH is 6.3-6.5 and thus provides the acidity to generate microbicidal levels of NO.

In one embodiment, for treating diseases other than CF, NaNO$_2$ is administered with a buffer such as 50 mM potassium phosphate, pH 6.5 as a diluent.

In one embodiment, the composition further comprises one or more pharmaceutically or physiologically acceptable carriers, diluents or excipients.

In one embodiment, the administration is aerosol, topical, oral, nasal, intravenous, intracranial, intraperitoneal, subcutaneous, intravesicular or intramuscular administration.

In one embodiment, the administration is by inhalation.

In one embodiment, the composition is provided as a dry powder form for administration by inhalation.

In one embodiment, the composition is provided as a nebulized solution form for administration by inhalation.

In one embodiment, the administration is by topical administration.

In one embodiment, the composition is provided as a paste form for topical administration.

In one embodiment, the composition is provided as a gel form for topical administration.

In one embodiment, the composition is provided as petroleum gel form for topical administration.

In one embodiment, composition is administered at least twice, at least 3 times, at least 4 times, at least 5 times, at least 6 times, at least 7 times, at least 8 times, or more than 8 times daily.

In one embodiment, composition is administered twice daily.

In one embodiment, the composition is administered about 2 to about 8, about 4 to about 8, or about 6 to about 8 times daily.

BRIEF DESCRIPTION OF DRAWINGS

FIG. 1 shows that mucoid PA CF isolate known as FRD1 is selectively killed by A-NO$_2^-$ in a pH-dependent manner. FIG. 1A-FIG. 1B provide graphs showing the effect of A-NO$_2^-$—on anaerobic growth of PA strains. FIG. 1C provides images showing A-NO$_2^-$ sensitivity of FRD1 or FRD1/pmucA as a function of pH. FIG. 1D-FIG. 1E provides photomicrographs showing the effect of A-NO$_2^-$ on anaerobic microfilms where the red bacteria are dead and the green bacteria are alive. FIG. 1F-FIG. 1G provide graphs showing the effects of A-NO$_2^-$ on colony forming units (CFU). FIG. 1H provides a graph showing competitive inhibition of A-NO$_2^-$ on colony growth.

FIG. 3 provides checkerboard assay MIC and associated FIC scores for *P. aeruginosa* for aerobic (FIG. 3A) and anaerobic (FIG. 3B) conditions.

FIG. 6 provides checkerboard assay MIC and associated FIC scores for *S. aureus* for aerobic (FIG. 6A) and anaerobic (FIG. 6B) conditions.

FIG. 7 provides checkerboard assay MIC and associated FIC scores for *S. typhimirium* for aerobic (FIG. 7A) and anaerobic (FIG. 7B) conditions.

FIG. 8 provides checkerboard assay MIC and associated FIC scores for *P. mirabilis* for aerobic (FIG. 8A) and anaerobic (FIG. 8B) conditions.

FIG. 9 provides checkerboard assay MIC and associated FIC scores for *Corynebacterium* spp. for aerobic (FIG. 9A) and anaerobic (FIG. 9B) conditions.

FIG. 10 provides checkerboard assay MIC and associated FIC scores for *A. baumannii* for aerobic conditions.

FIG. 11 provides checkerboard assay MIC and associated FIC scores for *E. cloacae* for aerobic (FIG. 11A) and anaerobic (FIG. 11B) conditions.

FIG. 12 provides checkerboard assay MIC and associated FIC scores for *E. faecalis* for aerobic (FIG. 12A) and anaerobic (FIG. 12B) conditions.

FIG. 13 provides checkerboard assay MIC and associated FIC scores for *S. epidermidis* for aerobic (FIG. 13A) and anaerobic (FIG. 13B) conditions.

FIG. 16 provides checkerboard assay MIC and associated FIC scores for *S. pyrogenes* for aerobic (FIG. 16A) and anaerobic (FIG. 16B) conditions.

FIG. 17 provides checkerboard assay MIC and associated FIC scores for *M. smegmatis* for aerobic conditions.

FIG. 18 provides a table summarizing the results of the FIC study summarizing synergy.

FIG. 19 provides a table summarizing the concentrations at FIC relevant to current treatment concentrations.

FIG. 20 provides checkerboard assay MIC and associated FIC scores for tobramycin for aerobic (FIG. 20A and FIG. 20B) and anaerobic (FIG. 20C and FIG. 20D) conditions with and without a nitrite background (7.5 mM).

FIG. 21 provides checkerboard assay MIC and associated FIC scores for ciprofloxacin for aerobic (FIG. 21A and FIG. 21B) and anaerobic (FIG. 21C and FIG. 21D) conditions with and without a nitrite background (7.5 mM).

FIG. 22 provides checkerboard assay MIC and associated FIC scores for ticarcillin for aerobic (FIG. 22A and FIG. 22B) and anaerobic (FIG. 22C and FIG. 22D) conditions with and without a nitrite background (7.5 mM).

FIG. 23 provides checkerboard assay MIC and associated FIC scores for colistin for aerobic (FIG. 23A and FIG. 23B) and anaerobic (FIG. 23C and FIG. 23D) conditions with and without a nitrite background (7.5 mM).

FIG. 24 provides checkerboard assay MIC and associated FIC scores for azithromycin for aerobic (FIG. 24A and FIG. 24B) and anaerobic (FIG. 24C and FIG. 24D) conditions with and without a nitrite background (7.5 mM).

FIG. 25 provides checkerboard assay MIC and associated FIC scores for sulfamethazine for aerobic (FIG. 25A and FIG. 25B) and anaerobic (FIG. 25C and FIG. 25D) conditions with and without a nitrite background (7.5 mM).

FIG. 26 provides checkerboard assay MIC and associated FIC scores for sulfamethoxazole for aerobic (FIG. 26A and FIG. 26B) and anaerobic (FIG. 26C and FIG. 26D) conditions with and without a nitrite background (7.5 mM).

FIG. 29 provides checkerboard assay MIC and associated FIC scores for imipenem for aerobic (FIG. 29A and FIG. 29B) and anaerobic (FIG. 29C and FIG. 29D) conditions with and without a nitrite background (7.5 mM).

FIG. 31 provides a summary of the FIC values showing synergy for the artificial urine media and the volunteer urine samples.

DETAILED DESCRIPTION OF THE INVENTION

Definitions

Figures 2A, 2B, 2C, 2D:
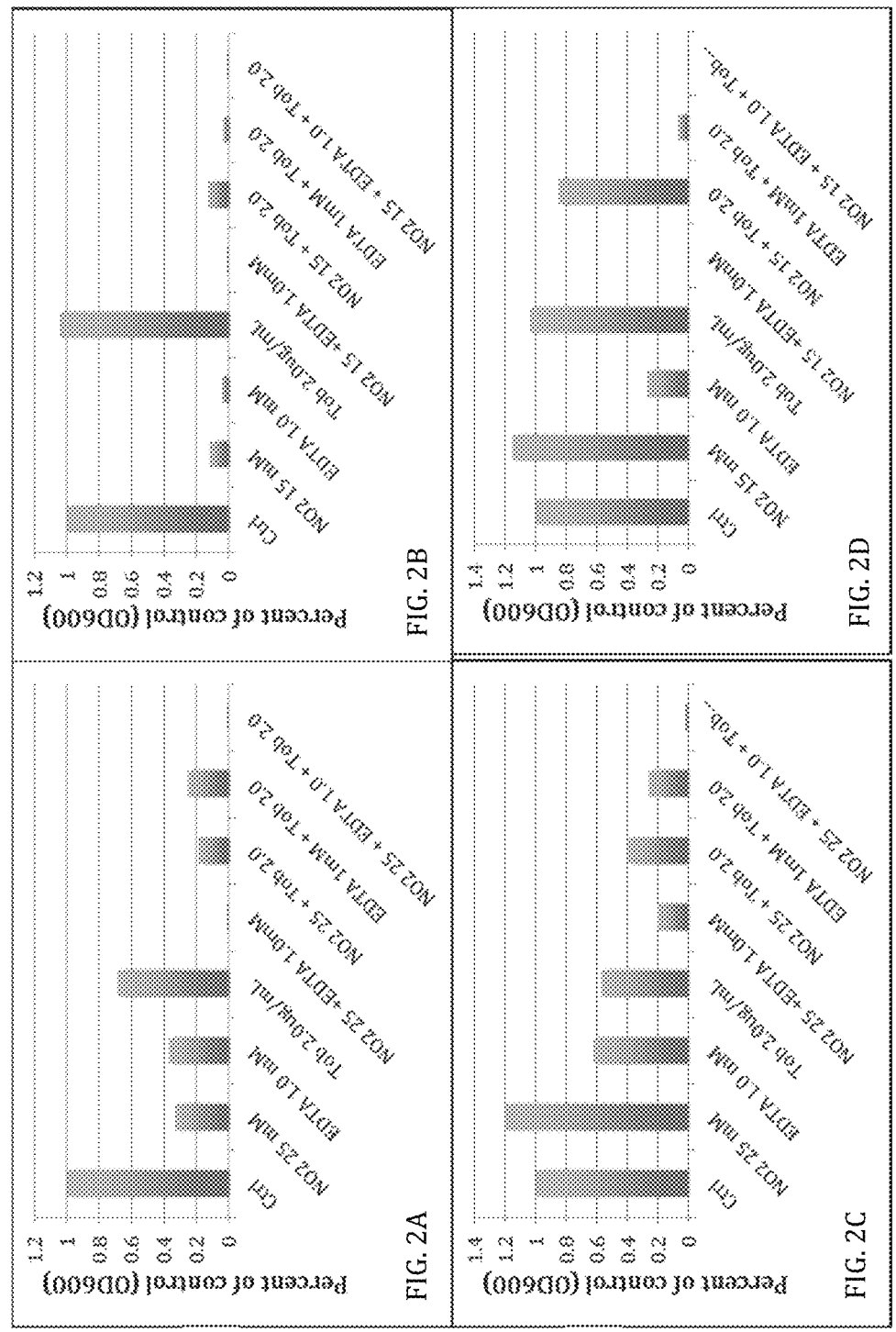
FIG. 2 provides graphs showing the effect of A-NO$_2^-$, EDTA and/or tobramycin on viability of PA strain PAO1 grown under aerobic conditions for 24 hr (FIG. 2A) or 48 hr (FIG. 2C) or grown under anaerobic conditions for 24 hr (FIG. 2B) or 48 hr (FIG. 2D).

All technical and scientific terms used herein, unless otherwise defined below, are intended to have the same meaning as commonly understood by one of ordinary skill in the art. References to methods employed herein are intended to refer to the methods as commonly understood in the art, including variations on those methods or substitutions of equivalent methods that would be apparent to one of skill in the art.

As used in this specification, the singular forms "a", "an" and "the" specifically also encompass the plural forms of the terms to which they refer, unless the content clearly dictates otherwise. For example, reference to "antimicrobial" includes mixtures of antimicrobials.

The term "infection" as used herein means and/or colonization by a microorganism and/or multiplication of a micro-organism, in particular, a bacterium. The bacterium can be gram negative such as the *Pseudomonas* genus, or gram positive *S. aureus* in a subject. Such infection may be unapparent or result in local cellular injury. The infection may be localized, subclinical and temporary or alternatively may spread by extension to become an acute or chronic clinical infection. The infection may also be a past infection wherein residual antigen from a protein associated with anaerobic growth of *P. aeruginosa*, or alternatively, reactive host antibodies that bind to isolated from a protein of *P. aeruginosa* protein or peptides there from, remain in the host. The infection may also be a latent infection, in which the microorganism is present in a subject, however the subject does not exhibit symptoms of disease associated with the organism. Preferably, the infection is a respiratory infection by *P. aeruginosa*, i.e., an infection of the respiratory tract. However, the term infection also encompasses a *P. aeruginosa* infection of a wound (e.g., a burn), an infection of the meninges (e.g., meningitis), a urinary tract infection, an infection of a heart valve (e.g., endocarditis), an ear infection, an eye infection, a bone infection (e.g., Vertebral osteomyelitis), a skin infection or a gastro-intestinal infection.

The term "bacterial-infection associated disease" shall be taken to mean a disease where the underlying pathology of the disease is a result of infection by one or more bacteria.

The term "respiratory tract" shall be taken to mean a system of cells and organs functioning in respiration, in particular the organs, tissues and cells of the respiratory tract include, lungs, nose, nasal passage, paranasal sinuses, nasopharynx, larynx, trachea, bronchi, bronchioles, respiratory bronchioles, alveolar ducts, alveolar sacs, alveoli, pneumocytes (type 1 and type 2), ciliated mucosal epithelium, mucosal epithelium, squamous epithelial cells, mast cells, goblet cells, and intraepithelial dendritic cells.

The term "subject" or "individual" or "patient" is meant to include any subject, particularly a mammalian subject, for whom diagnosis, prognosis, or therapy is desired The term a "therapeutically effective amount" as used herein means an amount of the composition, which when administered according to a desired dosage regimen, is sufficient to at least partially attain the desired therapeutic effect, or delay the onset of, or inhibit the progression of, halt, partially or fully the onset or progression of the infection or is able to reverse or partially reverse the antimicrobial sensitivity of the pathogenic microbe(s).

The term a "preventative effective amount" as used herein means an amount of the composition, which when administered according to a desired dosage regimen, is sufficient to at least partially prevent or delay the onset of the infection.

As used herein, "treating" or "treatment" refers to inhibiting the disease or condition, i.e., arresting or reducing its development or at least one clinical or subclinical symptom thereof. "Treating" or "treatment" further refers to relieving the disease or condition, i.e., causing regression of the disease or condition or at least one of its clinical or subclinical symptoms. The benefit to a patient to be treated is either statistically significant or at least perceptible to the patient and/or the physician. In the context of treating a bacterial infection, the term treatment includes reducing or eliminating colonization by a bacteria and/or multiplication of a bacteria including reducing biofilm formation or disrupting existing biofilms.

As used herein, the term "administering" refers to a method of giving a dosage of a pharmaceutical composition of the invention to a subject. The compositions utilized in the methods described herein can be administered by a route selected from, e.g., parenteral, dermal, transdermal, ocular, inhalation, buccal, sublingual, perilingual, nasal, rectal, topical administration, intravesicular and oral administration. Specific administration methods are described in further detail herein. Parenteral administration includes intravenous, intraperitoneal, subcutaneous, intraarterial, intravascular, and intramuscular administration. The preferred method of administration can vary depending on various factors (e.g., the components of the composition being administered and the severity of the condition being treated).

Accordingly, the present invention is directed toward novel methods for treatment of bacterial infections.

According to a fourth aspect of the invention there is provided a method for treating an individual suffering from a bacterial infection caused by a Gram-negative and/or Gram-positive bacteria.

In various embodiments, the bacterial infection is caused by pathogenic bacteria. Examples of pathogenic bacteria include, but are not limited to, members of genera *Escherichia, Salmonella, Listeria, Campylobacter, Shigella, Brucella, Helicobactor, Mycobacterium, Streptococcus, Staphylococcus,* and *Pseudomonas.*

In certain embodiments the pathogenic bacteria is one or more of *Bacillus* (*Bacillus anthracis*), *Bordetella* (*Bordetella pertussis*), *Borrelia* (*Borrelia burgdorferi*), *Brucella* (*Brucella abortus, Brucella canis, Brucella melitensis, Brucella suis*), *Campylobacter* (*Campylobacter jejuni*), *Chlamydia* and *Chlamydophila* (*Chlamydia* pneumonia, *Chlamydia trachomatis, Chlamydophila psittaci*), *Clostridium* (*Clostridium botulinum, Clostridium difficile, Clostridium perfringens, Clostridium tetani*), *Corynebacterium* (*Corynebacterium diphtheria*), *Enterococcus* (*Enterococcus faecalis, Enterococcus faecium*), *Escherichia* (*Escherichia coli*), *Francisella* (*Francisella tularensis*), *Haemophilus* (*Haemophilus influenza*), *Helicobacter* (*Helicobacter pylori*), *Legionella* (*Legionella pneumophila*), *Leptospira* (*Leptospira interrogans*), *Listeria* (*Listeria monocytogenes*), *Mycobacterium* (*Mycobacterium leprae, Mycobacterium tuberculosis, Mycobacterium ulcerans*), *Mycoplasma* (*Mycoplasma pneumonia*), *Neisseria* (*Neisseria gonorrhoeae, Neisseria meningitides*), *Pseudomonas* (*Pseudomonas aeruginosa*), *Rickettsia* (*Rickettsia rickettsii*), *Salmonella* (*Salmonella*

*typhi, Salmonella typhimurium), Shigella (Shigella sonnei), Staphylococcus (Staphylococcus aureus, Staphylococcus epidermidis, Staphylococcus saprophyticus), Streptococcus (Streptococcus agalactiae, Streptococcus pneumonia, Streptococcus pyogenes), Treponema pallidum, Vibrio (Vibrio cholera),* and *Yersinia (Yersinia pestis).* Examples of antibiotic resistant pathogenic bacteria include: various strains of *Staphylococcus aureus* (e.g., methicillin-resistant *Staphylococcus aureus*; MRSA), *Streptococcus pyogenes, Enterococcus faecium, Pseudomonas aeruginosa, Clostridium difficile, E. coli, Salmonella,* and *Acinetobacter baumannii.* Examples of Gram negative pathogenic bacteria include, but are not limited to *Acinetobacter calcoaceficus, Aeromonas hydrophile, Enterobacter aerogenes, Escherichia coli* ML-35, *Escherichia coli* O157:H7, *Pseudomonas putida, Pseudomonas* spp, *Proteus mirabilis, Providencia stuartii, Salmonella, Salmonella Michigan, Salmonella Gaminola, Salmonella Montbidea, Salmonella Poona, Vibrio* 01, *Vibrio vulnificus* CMCP6, *Vibrio vulnificus* M06, *Vibrio* sp., *Vibrio parahaemolyticus* P5, and the like.

In various embodiments, the bacteria is selected from *P. aeruginosa, E. coli, K. pneumoniae, S. maltophila, A. baumannii, P. mirabilis, B. cepacia, S. typhimurium, E. cloacae, H. pylori, S. aureus, S. epidermidis, B. anthracis, E. faecalis, S. pyrogenes, L. monocytogenes, Stretomyces* spp., *Nocardia* spp., *Corynebacterium,* or *M. smegmatis*

The infection may be, for example, an infection of lungs, skin, bones, joints, stomach, intestines, eye, CNS, blood, or urinary tract including but not limited to a lung infection, an ocular infection, a burn, a wound, a skin infection, a blood borne infection, or a combination of two or more of said infections.

In other embodiments, the infection is selected from an infection of the urinary tract, gastrointestinal system, kidney, liver, blood, bones, or central nervous system.

In various embodiments, the bacterial infection can result in a disease state that include, but are not limited to bacteremia, upper and lower respiratory tract infections, skin and soft-tissue infections, urinary tract infections (UTIs), endocarditis, intra-abdominal infections, septic arthritis, osteomyelitis, CNS infections, and ophthalmic infections.

One embodiment is specifically directed to *Pseudomonas* (e.g., PA) infections.

In exemplary embodiment, the infection is a PA infection of the respiratory tract. In one particular embodiment, the methods are suitable for treatment of respiratory tract infections in individuals diagnosed with CF. In one particular embodiment, the methods are suitable for treatment of respiratory infections in individuals diagnosed with COPD.

In additional embodiments, the present invention is directed to treatment of a bacterial respiratory tract infection caused at least in part by *P. aeruginosa* of a mucoid type and/or *Staphylococcus aureus.* In further embodiments, a method according to the invention is for treating such an infection in an individual diagnosed with pulmonary disease. In another embodiment, a method according to the invention is for treating a bacterial respiratory tract infection in an individual diagnosed with chronic obstructive pulmonary disease.

The various embodiments of the invention described herein may suitably comprise, consist essentially of, or consist of, A-NO$_2^-$, at least one iron chelating agent, and at least one antibiotic agent.

In certain embodiments, the antibiotic agent is selected from aminoglycosides, tetracyclines, sulfonamides, fluoroquinolones, macrolides, oxazolidinones, monobactams, cephalosporins, penicillins, polymyxins, glycylcyclines, and lincosamides.

In certain embodiments of the invention, the composition may comprise, consist essentially of, or consist of A-NO$_2^-$, EDTA and at least one aminoglycoside antibiotic.

In certain other embodiments of the invention, the composition may comprise, consist essentially of, or consist of A-NO$_2^-$, EDTA and tobramycin.

In one embodiment, the acidified nitrite (A), an iron chelator agent (C), and an antibiotic agent (Ab) are provided in a ratio (A:C:Ab) of about 10-600:1-100:0.01-6000, about 30-600:1-100:0.01-6000, about 30:1:0.01, about 300:1:0.01, about 600:1:0.01, about 30:10:0.01, about 30:100:0.01, about 30:1:0.1, about 30:1:1, about 30:1:10, about 30:10:100, about 30:10:1000, or about 30:10:6000.

Synergistic Activity

Surprisingly, the combination of A-NO$_2^-$, a chelating agent and an antibiotic agent has been shown to have synergistic effects such that reduced dosages of each agent are required for therapeutic efficacy. In exemplary embodiment, a reduced dosage of the antibiotic agent is permissible. This combination is effective at reducing viability of the bacteria under aerobic conditions, anaerobic, or both aerobic and anaerobic conditions. The compositions and methods described herein provide reduced dosages with improve side effect profiles, increased safety and by extension patient compliance of the therapy, and reduce cost of treatment. Patient compliance is of particular importance because the regimen entails taking a dosage of each of the three components (A-NO$_2^-$ EDTA-tobramycin) recommended by the treating physician for 4-5 times per day by aerosol for a period of at least 14 days or until desired beneficial effect (e.g., increased FEV$_1$, PFT levels for respiratory function).

The reduced dosage of aminoglycoside antibiotic in the formulations disclosed herein have a beneficial improved safety profile over typically administered. All amino glycosides are nephrotoxic, and neurotoxic, with neurotoxicity reported as both auditory and vestibular ototoxicity. Aminoglycosides are nephrotoxic because a small but sizable proportion of the administered dose (≈5%) is retained in the epithelial cells lining the S1 and S2 segments of the proximal tubules (Vandewalle, A., et al., Kidney Int. 19:529-539 (1981)) after glomerular filtration (Fabre, J. et al., Kidney Int. 10:444-449 (1976)). The aminoglycoside antibiotic tobramycin has caused kidney problems, nerve damage, or permanent hearing loss, even at usual doses. The low level of aminoglycoside antibiotic in the formulations described herein is believed to potentiate the therapeutic activity of A-NO$_2^-$ and the chelator agent without the toxic side effect profile that exists at standard doses.

Acidified Nitrite

The compositions described herein comprise acidified nitrite.

The methods according to the present invention comprise administering a therapeutically effective amount of an acidified nitrite (A-NO$_2^-$) composition, for example in a solution form, having a pH of less than 7 to the individual. In more specific embodiments, the nitrite composition has a pH of about 5.5-6.5, has a pH of about 6.5, or has a pH of about 5.5.

Acidified nitrite has been previously shown to be selective for killing bacterial, for example but not limited to, mucoid *P. aeruginosa* bacteria (U.S. Pat. No. 8,557,300) as well as *S. aureus* and *B. cepacia* (Major 2010 reference Infection and immunity). Mixed cultures of mucoid and nonmucoid PA were mixed and treated with anaerobic 15 mM NO$_2^-$, pH of 6.5, after which CFU are measured. After 5 days, mucoid FRD1 consistently lost viability at three different bacterial ratios tested (*=<$10^3$ CFU/ml), while non-mucoid FRD1/pmucA maintained viability. $NO_2^-$ may be an effective therapeutic agent against mucoid PA in cases where the pH of CF airway surface liquid is slightly acidic. In one particular embodiment, the pH is 6.5.

The nitrite may be administered to the individual via any suitable route or device. In one embodiment, the nitrite is administered via a nebulizer (an inhaler). The most common form of delivery will be as a mist where the sodium nitrite salts is immediately dissolved in the hydrated airway mucus, unlike gaseous nitric oxide. Thus, this method of delivery allows better penetration of the solution to the bacteria embedded in the biofilm as compared to a gas. Aerosol delivery systems typically contain concentrations of a nebulized agent that are about 25-fold higher than the effective killing dose in airway surface liquid (ASL). In another embodiment, the nitrite is administered in dry powder form via crushed powder delivery systems. In a preferred embodiment, the powder is administered through inhalation.

The nitrite composition is administered in an amount that will effectively treat the bacterial respiratory tract infection i.e., a therapeutically effective amount. Therapeutic amounts will vary based on an individual's age, body weight, symptoms and the like, and may be determined by one of ordinary skill in the art in view of the present disclosure.

In various embodiments, the A-$NO^{2-}$ is administered as a sodium salt, potassium salt, magnesium salt, or calcium salt.

In one embodiment, the A-$NO^{2-}$ is administered as $NaNO_2$.

In one embodiment, $NaNO_2$ adjusted to pH 6.5 in non-CF lung disease.

In one embodiment, the therapeutically effective amount of nitrite is sufficient to allow at least about 3 mM of nitrite to reach the bacterial respiratory tract infection site.

In one embodiment, 3 mM $NO_2^-$ can typically generate sufficient NO to kill 50% of the mucA mutant PA in the CF airways while 15-20 mM $NO_2^-$ can typically kill approximately 100%, even in the absence of or reduced expression of human iNOS. Thus, for treatment of mucoid, mucA mutant PA, the aerosol theoretically may, in one embodiment, contain about 375 mM $NO_2^-$ at about pH 6.5 (or lower) to deliver about 15 mM $NO_2^-$ to CF ASL. Acidified $NO_2^-$ delivered in such doses to the CF ASL will kill mucoid PA without harming airway epithelia or disrupting key physiological lung functions.

In one embodiment, the therapeutically effective amount of A-$NO_2^-$ is between about 5 and about 300 mM, between about 5 and about 200 mM, between about 5 and about 100 mM, between about 10 and about 300 mM, between about 10 and about 200 mM, between about 10 and about 100 mM, between about 15 and about 300 mM, between about 15 and about 200 mM, or between about 15 and about 100 mM.

In one embodiment, the therapeutically effective amount of A-$NO_2^-$ is between about 5 and about 50 mM, between about 5 and about 40 mM, between about 5 and about 30 mM, between about 5 and about 20 mM, or between about 5 and about 10 mM.

In one embodiment, the therapeutically effective amount of A-$NO_2^-$ is between about 10 and about 50 mM, between about 10 and about 40 mM, between about 10 and about 30 mM, or between about 10 and about 20 mM.

In one embodiment, the therapeutically effective amount of A-$NO_2^-$ is between about 15 and about 50 mM, between about 15 and about 40 mM, between about 15 and about 30 mM, or between about 15 and about 20 mM.

In one embodiment, the therapeutically effective amount of A-$NO_2^-$ is about 15 mM for anaerobic growth.

In one embodiment, the therapeutically effective amount of A-$NO_2^-$ is about 25 mM for aerobic growth.

In another embodiment, a 50 mM potassium phosphate buffer, pH 6.5 is used.

Iron Chelator

The compositions described herein comprise at least one iron chelator.

Iron is crucial to many important physiologic functions in microbial pathogens, including energy production, oxygen transport, and the regulation of gene expression. Iron also promotes biofilm formation on abiotic surfaces (e.g., plastic), in part by regulating surface motility and by stabilizing the biofilm polysaccharide matrix (Singh P. *Biometals* 2004; 17:267-270; Singh P K, et al., *Nature* 2002; 417:552-555; Patriquin G M, et al., *J Bacteriol* 2008; 190:662-671; Banin E, et al., Proc Natl Acad Sci USA 2005; 102:11076-11081; Berlutti F, et al., *Int J Immunopathol Pharmacol* 2005; 18:661-670). Enhanced iron release from human CF airway epithelial cells also promotes robust *P. aeruginosa* biofilm formation on mucus-producing and non-mucus-producing CF airway epithelial cells (Moreau-Marquis S, et al., *Am J Physiol Lung Cell Mol Physiol* 2008; 295:L25-L37).

In at least one embodiment, the iron chelator agent is selected from the group consisting of citric acid, phosphates, the di-, tri- and tetra-sodium salts of ethylene diamine tetraacetic acid (EDTA), ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochioride (TRIEN), diethylenetriamin-pentaacetic acid (DPTA), triethylenetetramine hexaacetic acid (TTG), deferoxamine (DFO), deferasirox (DSX), Dimercaprol, zinc citrate, penicilamine succimer, Editronate, sodium hexmetaphosphate and edetate calcium disodium and combinations thereof.

In one embodiment, the iron chelator agent is selected from the group consisting of citric acid, phosphates, the di-, tri- and tetra-sodium salts of ethylene diamine tetraacetic acid (EDTA), ethylene glycol-bis-(b-aminoethylether)-N,N,N',N'-tetraacetic acid (EGTA); 1,2-bis(2-aminophenoxy)ethane-N,N,N',N'-tetraacetic acid (BAPTA); ethylene-N,N'-diglycine (EDDA); 2,2'-(ethylendiimino)-dibutyric acid (EBDA); lauroyl EDTA; dilauroyl EDTA, triethylene tetramine dihydrochioride (TRIEN), diethylenetriamin-pentaacetic acid (DPTA), triethylenetetramine hexaacetic acid (TTG), deferoxamine (DFO), deferasirox (DSX), Dimercaprol, zinc citrate, penicilamine succimer, Editronate, sodium hexmetaphosphate and edetate calcium disodium and combinations thereof.

In one embodiment, the iron chelator agent is ethylene diamine tetraacetic acid (EDTA).

In one embodiment, the iron chelator agent is deferoxamine (DFO).

In one embodiment, the iron chelator agent is deferasirox (DSX).

In one embodiment, the iron chelator is a di-, tri- or tetra-sodium salt of the iron chelator. In one embodiment, the iron chelator is the di-sodium salt of EDTA.

In one embodiment, the therapeutically effective amount of the chelator is between about 0.1 and about 50 mM, between about 0.1 and about 30 mM, between about 0.1 and about 10 mM, or between about 0.1 and about 5 mM.

In one embodiment, the therapeutically effective amount of the chelator is between about 0.5 and about 50 mM, between about 0.5 and about 30 mM, between about 0.5 and about 10 mM, or between about 0.5 and about 5 mM.

In one embodiment, the therapeutically effective amount of the chelator is between about 1 and about 50 mM, between about 1 and about 30 mM, between about 1 and about 10 mM, or between about 1 and about 5 mM.

In one embodiment, the therapeutically effective amount of the chelator is between about 5 and about 50 mM, between about 5 and about 30 mM, between about 5 and about 10 mM, or between about 5 and about 5 mM.

In one embodiment, the therapeutically effective amount of the chelator is about 0.5 mM.

In at least one particular embodiment, the iron chelator agent is the di-, tri- or tetra-sodium salt of ethylene diamine tetraacetic acid (EDTA). In at least one embodiment, the metal ion chelating agent is the di-sodium salt of EDTA. In one embodiment, the di-sodium salt of EDTA is calcium di-sodium EDTA.

In some embodiments, the EDTA is present in the composition at a concentration of from between 5% (wt/wt) to 100% (wt/wt). In some embodiments, the EDTA is from between 25% (wt/wt) to 85% (wt/wt). In some embodiments, the EDTA is present from between 50% (wt/wt) to 65% (wt/wt).

Antibiotic Agents

The compositions described herein comprise at least one antibiotic agent.

Accordingly, the invention provides compositions that include a formulation described herein, or a specific compound described herein, in combination with a second antibacterial agent.

Other classes of antibacterial agents that can act synergistically when combined with a compound described herein for the treatment of a bacterial infection include aminoglycosides, tetracyclines, sulfonamides, fluoroquinolones, macrolides, oxazolidinones, monobactams, cephalosporins, penicillins, polymyxins, glycylcyclines, and lincosamides.

Of particular use in the compositions described herein are aminoglycoside antibiotics. In one embodiment, at least one aminoglycoside antibiotic and combinations thereof are used in the compositions described herein.

In one embodiment, the aminoglycoside antibiotic is selected from kanamycin A, amikacin, arbekacin, bekanamycin, tobramycin, dibekacin, spectinomycin, hygromycin B, verdamicin, astromycin, gentamicin, sisomicin, netilmicin, neomycins B, C, neomycin E (paromomycin), framycetin, ribostamycin, dihydrostreptomycin, or streptomycin.

In one embodiment, the aminoglycoside antibiotic is tobramycin (CAS#32986-56-4).

Other antibacterial agents that can also be used in the compositions described herein include, but are not limited to penicillins such as amoxicillin, ampicillin, azlocillin, mezlocillin, apalcillin, hetacillin, bacampicillin, carbenicillin, sulbenicillin, ticarcillin, azlocillin, mecillinam, pivmecillinam, methicillin, ciclacillin, talampicillin, aspoxicillin, oxacillin, cloxacillin, dicloxacillin, flucloxacillin, nafcillin, pivampicillin; cephalosporins such as cephalothin, cephaloridine, cefaclor, cefadroxil, cefamandole, cefazolin, cephalexin, cephradine, ceftizoxime, cefoxitin, cephacetrile, cefotiam, cefotaxime, cefsulodin, cefoperazone, ceftizoxime, cefmenoxime, cefmetazole, cephaloglycin, cefonicid, cefodizime, cefpirome, ceftazidime, ceftriaxone, cefpiramide, cefbuperazone, cefozopran, cefoselis, cefluprenam, cefuzonam, cefepime, cefpimizole, cefclidin, cefixime, ceftibuten, cefdinir, cefpodoxime axetil, cefpodoxime proxetil, cefteram pivoxil, cefetamet pivoxil, cefcapene pivoxil cefditoren pivoxil, cefuroxime, cefuroxime axetil, latamoxef and pharmaceutically acceptable salts, solvates or prodrugs thereof; monobactams such as aztreonam or carumonam or a pharmaceutically acceptable salt, solvate or prodrug thereof; glycylcyclines such as tigecycline or a pharmaceutically acceptable salt, solvate or prodrug thereof; aminoglycosides, including, but not limited to, amikacin, gentamicin, kanamycin, neomycin, netilmicin, paromomycin, streptomycin, tobramycin and pharmaceutically acceptable salts, solvates or prodrugs thereof; carbapenems, including, but not limited to, imipenem, biapenem, meropenem, ertapenem, faropenem, doripenem, panipenem, PZ-601 and pharmaceutically acceptable salts, solvates or prodrugs thereof; macrolide, including, but not limited to, erythromycin, azithromycin, dirithromycin, telithromycin, clarithromycin and pharmaceutically acceptable salts, solvates or prodrugs thereof; fluoroquinolones, including, but not limited to, levofloxacin, ciprofloxacin, ofloxacin, gatifloxacin, norfloxacin, moxifloxacin, trovafloxacin and pharmaceutically acceptable salts, solvates or prodrugs thereof; acylamino-penicillins, such as piperacillin or a pharmaceutically acceptable salt, solvate or prodrug thereof; tazobactam or a pharmaceutically acceptable salt, solvate or prodrug thereof; daptomycin or a pharmaceutically acceptable salt, solvate or prodrug thereof.

In one embodiment, the antibiotic agent is selected from Tobramycin, Azithromycin, Colistin, Ticarcillin, Ciprofloxacin, Sulfametoxazole, Sulfamethazine, Tetracycline, Vancomycin, Imipenem, Cefepime or a pharmaceutically acceptable salt, solvate or prodrug thereof;

In one embodiment, the combined use of tobramycin and FDA-approved iron chelators may be an effective therapy to treat patients with CF and other lung disease characterized by antibiotic-resistant P. aeruginosa biofilms but not in combination with $A-NO_2^-$. (Moreau-Marquis et al., Am J Respir Cell Mol Biol. 2009 September; 41(3): 305-313)

The amount of antibiotic agent in the compositions of the present invention can vary depending on the total overall volume of the formulation and the concentration of the other components. However, the amount of the antibiotic agent in the formulation will generally range from about 0.001 to about 1.5% w/v, and includes from about 0.005 to about 0.5% w/v, from about 0.001 to about 0.1% w/v, from about 0.01 to about 0.1% w/v, and from about 0.1 to about 1% w/v. In particular embodiments, the amount of the antibiotic agent in the formulation will be about 0.1, 0.2, or 0.4% w/v. Where a chelating agent is used as the antibiotic agent, the amount of chelating agent in the formulation will generally range from about 0.001% to about 0.5% w/v. The antibiotic agent may comprise one, or more than one agent, such as two, three, four, etc., different antibiotic agents.

In certain embodiments related to the use of the compositions described herein for treating and/or preventing bacterial-infection associated disease, the at least one antibiotic agent is present in quantities ranging from between 0.000001% (wt/wt) to about 5.0% (wt/wt) of said composition. In certain embodiments related to the use of the compositions described herein for treating and/or preventing bacterial-infection associated disease, the at least one antibiotic agent is present at 0.002% (wt/wt) of said composition.

In certain embodiments related to the use of the compositions described herein for treating and/or preventing PA-infection associated disease, the at least one antibiotic agent is present in quantities ranging from between 0.000001% (wt/wt) to about 5.0% (wt/wt) of said composition. In certain embodiments related to the use of the compositions described herein for treating and/or preventing PA-infection associated disease, the at least one antibiotic agent is present at 0.002% (wt/wt) of said composition.

An attending physician, depending on the severity as well as the general age, health and weight of the subject being treated and type of bacterial-infection associated disease, can determine the therapeutically effective amount or the preventative effective amount and type of the at least antibiotic agent.

In one embodiment, the aminoglycoside antibiotic is tobramycin.

In one embodiment, the therapeutically effective amount of antibiotic is between about 0.001 mM and about 300 mM, between about 0.001 mM and about 200 mM, between about 0.001 mM and about 100 mM, between about 0.001 mM and about 10 mM, between about 0.001 mM and about 1 mM, between about 0.001 mM and about 0.5 mM, between about 0.001 mM and about 0.1 mM, or between about 0.001 mM and about 0.01 mM.

In one embodiment, the therapeutically effective amount of antibiotic is between about 0.003 mM and about 300 mM, between about 0.003 mM and about 200 mM, between about 0.003 mM and about 100 mM, between about 0.003 mM and about 10 mM, between about 0.003 mM and about 1 mM, between about 0.003 mM and about 0.5 mM, between about 0.003 mM and about 0.1 mM, or between about 0.003 mM and about 0.01 mM.

In one embodiment, the therapeutically effective amount of antibiotic is between about 0.005 mM and about 300 mM, between about 0.005 mM and about 200 mM, between about 0.005 mM and about 100 mM, between about 0.005 mM and about 10 mM, between about 0.005 mM and about 1 mM, between about 0.005 mM and about 0.5 mM, between about 0.005 mM and about 0.1 mM, or between about 0.005 mM and about 0.01 mM.

In one embodiment, the therapeutically effective amount of antibiotic is about 5 µM.

In one embodiment, the therapeutically effective amount of antibiotic is about 4.23 µM.

Pharmaceutical Formulations

The compositions described herein can be formulated in a variety of forms well known in the art, suitable for various modes of administration. Non-limiting examples of formulations in which the compositions described herein can be prepared as include inhaled powder, inhaled solution, oral gavage, intratracheal, oral solid, oral solution, irrigation solution or injectable formulations. The formulations of the compositions described herein can be prepared for administration by means known to those in the art.

The above-exemplified forms of the compositions described herein can be manufactured by methods well known to one of skill in the art of formulation science. Additionally, the compositions described herein may include other optional excipients to aid in the manufacturing and/or administration of the compositions described herein. Non-limiting examples of such excipients are well known in the art and include flavaourants, colorants, palatants, antioxidants, viscosity modifying, tonicity agents, drug carriers, sustained-release agents, comfort-enhancing agents, emulsifiers, solubilizing aids, lubricants, binding agents and other stabilizing agents to aid in the manufacturing and/or administration of the compositions.

In a particular embodiment, the present invention relates to formulations for administration by inhalation by means of dry powder inhalers. In particular, the present invention relates to dry powder formulations comprising a combination of $A\text{-}NO_2^-$, EDTA and tobramycin, the process for their preparation and use thereof for the prevention and/or treatment of bacteria-associated respiratory infections and diseases.

In one embodiment, the bacteria-associated respiratory infection or disease are a PA-associated respiratory infection or disease.

Tobramycin is available in an Dry Powder Inhalation (DPI) formulation (the Podhaler™, Novartis Pharmaceuticals Corporation, East Hanover, N.J., USA) and has been used for treating PA infection in cystic fibrosis. (Shteinberg and Elborn, Adv Ther. 2015 January; 32(1):1-9; VanDevanter, Med Devices (Auckl) 2011; 4: 179-188; U.S. Pat. Nos. 7,097,827, 7,368,102, 7,442,388, 7,516,741, 7,559,325, 8,069,851, 8,349,294, and 8,715,623). Four 28 mg cartridges are used with the Podhaler to provide the effective dose of 112 mg of tobramycin daily. In other studies, Tobramycin inhaled solution (TIS) is also effective when administered 112 mg twice daily, or 300 mg daily (Konstan et al., Pediatr Pulmonol. 2011 March; 46(3):230-8); Konstan et al., Journal of Cystic Fibrosis 10 (2011) 54-61). Common side effects at these dosages include headache, tinnitus and hearing loss which may impact patient compliance. Similar drug delivery technology for DPI and TIS may be modified to include effective amounts of $A\text{-}NO_2^-$ and chelating agent as described herein.

In one embodiment, the compositions described herein may be aqueous and contain 0-90% water. In other embodiments, the aqueous compositions described herein may contain 20-80% water. In still other embodiments, aqueous compositions may contain 50-70% water. The water may further comprise water that is plain, distilled, sterile, demineralized or deionized.

In one embodiment, the composition further comprises one or more pharmaceutically or physiologically acceptable carriers, diluents or excipients.

In one embodiment, the administration is aerosol, topical, oral, nasal, intravenous, intracranial, intraperitoneal, subcutaneous, intravesicular, or intramuscular administration.

In one embodiment, the administration is by inhalation.

In one embodiment, the composition is provided as a dry powder form for administration by inhalation.

In one embodiment, the composition is provided as a nebulized solution form for administration by inhalation.

In one embodiment, the administration is by topical administration.

In one embodiment, the topical administration includes direct application with sterile applicator such as cotton swabs, or after a brief debridement of decayed skin surrounding a wound or sore.

In one embodiment, the administration is by intravesicular administration.

In one embodiment, the composition is provided as a paste form for topical administration.

In one embodiment, the composition is provided as a gel form for topical administration.

In one embodiment, the composition is provided as petroleum gel form for topical administration.

Methods of Use

The present compositions are useful in treating a bacterial infection. Bacterial infection can occur in the lungs, skin, bones, joints, stomach, intestines, eye, CNS, blood, or urinary tract. Bacterial infections can result in disease states that include but are not limited to bacteremia, upper and lower respiratory tract infections, skin and soft-tissue infections, urinary tract infections (UTIs), endocarditis, intra-abdominal infections, septic arthritis, osteomyelitis, CNS infections, and ophthalmic infections.

In one embodiment, the pharmaceutical compositions described herein are specifically noted to have potent effectiveness against *Pseudomonas* infections, including *P. aeruginosa*. In one embodiment, the pharmaceutical compositions are especially useful in treating *P. aeruginosa* respiratory infections in patients with cystic fibrosis or chronic obstructive pulmonary disease.

Specifically relating to CF, chronic PA colonization in the lungs is a major cause of morbidity and mortality in CF patients (Dodd, Chronic Respiratory Disease 2.3 (2005): 139-49). Approximately 80% of adults with CF are permanently colonized by PA (Heijerman H., J Cyst Fibros 2005; 4:49-54). Once formed, these bacterial populations are difficult to treat, mainly due to the biofilm mode of growth where refractory organisms are enmeshed in thick airway mucus. This growth is associated with an increased frequency of mutations, as well as the adaption of PA to the inflammatory defense mechanisms in the lungs and antibiotic treatment. As a result, PA infections can persist for decades, while the lung tissue is gradually destroyed.

Mucoid, mucA mutant PA are sensitive to acidified nitrite ($A\text{-}NO_2^-$) in vitro and in vivo. The antibiotic-resistant mucoid form of PA are highly susceptible to $A\text{-}NO_2^-$, especially under anaerobic conditions (Yoon S S, et al. 2006. J. Clin. Invest. 116:436-446) and bacterial respiratory infections may be treated in an individual using acidified nitrite (U.S. Pat. No. 8,557,300 B2).

Other compounds are used for treating PA infections in patients with CF or COPD infections including the aminoglycoside antibiotic tobramycin, that has been shown to be effective in combination with an iron-chelator (Moreau-Marquis S, et al. 2009. Am J Respir Cell Mol Biol 41:305-313; Dal Negro R, et al. 2008. Adv Ther 25:1019-1030). However, a high level of resistance has been shown when bacteria are cultured on airway cells. (Moreau-Marquis S, et al., Am J Physiol Lung Cell Mol Physiol 2008; 295:L25-L37). Aminoglycoside antibiotics are known to have toxic side effects and tobramycin is not as effective at killing PA under anaerobic relative to aerobic conditions.

In one aspect, the present invention provides methods of treating bacterial infection comprising administering to a subject in need thereof a composition comprising effective amounts of:
 a) $A\text{-}NO2^-$;
 b) an iron chelator; and
 c) an antibiotic agent,
resulting in treatment of the bacterial infection.

In various embodiments, the bacterial infection is an infection of the skin, lungs, urinary tract, gastrointestinal system, kidney, liver, blood, bones, or central nervous system.

In one embodiment, the bacterial infection is a PA infection.

In one embodiment, the PA infection is an infection of the respiratory tract.

In one embodiment, treatment results in reduction or amelioration of a symptom is selected from the group consisting of bronchoconstriction, microbial infection, increased mucus secretion, pain, and decreased airflow.

In one embodiment, the bacterial infection is a *P. aeruginosa* infection.

In one embodiment, the *Pseudomonas* infection (e.g., *P. aeruginosa* infection) is a lung infection, an ocular infection, a burn infection, a wound infection, a skin infection, a blood infection, a bone infection, or a combination of two or more of said infections.

In one embodiment, the subject has been diagnosed with CF.

In one embodiment, the subject has been diagnosed with COPD.

In one embodiment, the subject has been diagnosed with bacterial pneumonia.

In one embodiment, the subject has been diagnosed with pressure ulcers.

In one embodiment, the subject has been diagnosed with diabetic foot ulcers.

In one embodiment, the subject has been diagnosed with acne or carbuncles.

In one embodiment, the subject has been diagnosed with a urinary tract infection.

In one embodiment, the subject has been diagnosed with CF and only $NaNO_2$ is administered without a diluent. The CF airway pH is 6.3-6.5 and thus provides the acidity to generate microbicidal levels of NO.

In one embodiment, for treating diseases other than CF, $NaNO_2$ is administered with a buffer such as 50 mM potassium phosphate, pH 6.5 as a diluent.

In one embodiment, the composition is administered parenterally, intranasally, intratracheally or by inhalation.

In one embodiment, the composition is administered by inhalation.

In one embodiment, the composition is administered in a dry powder form for inhalation.

In one embodiment, the composition is provided as a nebulized solution form for administration by inhalation.

In one embodiment, the administration is by topical administration.

In one embodiment, the administration is as a solution for bladder irrigation.

In one embodiment, the composition is provided as a paste form for topical administration.

In one embodiment, the composition is provided as a gel form for topical administration.

In one embodiment, the composition is provided as petroleum gel form for topical administration.

In one embodiment, the composition is administered at least twice, at least 3 times, at least 4 times, at least 5 times, at least 6 times, at least 7 times, at least 8 times, or more than 8 times daily.

In one embodiment, the composition is administered twice daily.

In one embodiment, about 2-8, about 4-8, or about 6-8 administrations are provided daily.

In one embodiment, the present invention provides a method of treating a condition associated with bacterial-infection comprising administering to a subject in need thereof a composition comprising effective amounts of:
 a. $A\text{-}NO2^-$;
 b. an iron chelator; and
 c. an antibiotic,
resulting in treatment of a condition associated with bacterial infection.

In one embodiment, the bacterial infection is selected from an infection of the skin, lungs, urinary tract, gastrointestinal system, kidney, liver, blood, bones, or central nervous system.

In one embodiment, the antibiotic is selected from aminoglycosides, tetracyclines, sulfonamides, fluoroquinolones, macrolides, oxazolidinones, monobactams, cephalosporins, penicillins, polymyxins, glycylcyclines, and lincosamides.

In one embodiment, the antibiotic is an aminoglycoside antibiotic.

In one embodiment, the present invention provides a method of inhibiting the growth of a bacterial biofilm, comprising administering to a subject in need thereof a composition comprising effective amounts of:
a. A-NO2⁻;
b. an iron chelator; and
c. an antibiotic,
resulting in inhibition of the growth of the bacterial biofilm, where the biofilm may be aerobic, anaerobic or a combination thereof.

In one embodiment, the bacterial infection is selected from an infection of the skin, lungs, urinary tract, gastrointestinal system, kidney, liver, blood, bones, or central nervous system.

In one embodiment, the antibiotic is selected from aminoglycosides, tetracyclines, sulfonamides, fluoroquinolones, macrolides, oxazolidinones, monobactams, cephalosporins, penicillins, polymyxins, glycylcyclines, and lincosamides.

In one embodiment, the antibiotic is an aminoglycoside antibiotic.

In one embodiment, the present invention provides a method of treating a condition associated with PA-infection comprising administering to a subject in need thereof a composition comprising effective amounts of:
a. A-NO2⁻;
b. an iron chelator; and
c. an antibiotic,
resulting in treatment of a condition associated with PA infection.

In one embodiment, the present invention provides a method of inhibiting the growth of a PA biofilm, comprising administering to a subject in need thereof a composition comprising effective amounts of:
a. A-NO2⁻;
b. an iron chelator; and
c. an antibiotic,
resulting in inhibition of the growth of the PA biofilm, where the biofilm may be aerobic, anerobic or a combination thereof.

Dosage

The pharmaceutical formulations are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art Particularly suitable dosage ranges are described herein. The dosage may also depend, without limitation, on the route of administration, the patient's state of health and weight, and the nature of the formulation.

The methods according to the present invention are particularly suitable for treating a bacterial respiratory tract infection in a CF individual caused by gram negative bacteria such as *Pseudomonas aeruginosa, Burkholderia cepacia* types, or *Staphylococcus aureus* gram positive bacteria. In additional embodiments, the methods according to the invention are suitable for treating bacterial respiratory infection caused by *Pseudomonas aeruginosa* of a mucoid type. A mucoid *Pseudomonas aeruginosa* is defined as an organism that overproduces the exopolysaccharide alginate. The production of alginate severely complicates the overall clinical course for CF patients and renders such organisms resistant to phagocytic cells and antibiotics.

Administration

Administration of the pharmaceutical compositions of the present invention can be by any of the routes known to one of skill in the art. Administration may be by, e.g., intramuscular injection. The compositions utilized in the methods described herein can also be administered by a route selected from, e.g., parenteral, dermal, transdermal, ocular, inhalation, buccal, sublingual, perilingual, nasal, rectal, intravesicular, topical administration, and oral administration. Parenteral administration includes intravenous, intraperitoneal, subcutaneous, and intramuscular administration. The preferred method of administration can vary depending on various factors, e.g., the components of the composition being administered and the severity of the condition being treated.

In addition, single or multiple administrations of the compositions of the present invention may be given to a subject.

Subjects who are particularly susceptible to certain bacterial infections may require multiple treatments to establish and/or maintain protection against a certain bacteria. For example, subjects who are particularly susceptible to *Pseudomonas* infection may require multiple treatments to establish and/or maintain protection against the bacteria. The dosages may then be adjusted or repeated as necessary to reduce or eliminate *Pseudomonas* infection.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein. All documents referenced herein are hereby incorporated by reference in their entirety.

The present invention will be more readily understood by referring to the following non-limiting examples, which are given to illustrate the invention rather than to limit its scope.

Example 1: Acidified Nitrite Selectively Kills Mucoid FRD1 *Pseudomonas Aeruginosa* in a pH Dependent Manner Some background data are provided in FIG. 1 and are representative of some of the data in the paper by Yoon et al., (Yoon S S, et al. 2006. J. Clin. Invest. 116:436-446). Upon anaerobic culture of PA at pH 6.5 (the pH of the CF airway surface liquid) with 15 mM $NO_3^-$ (alternative electron acceptor), mucoid PA CF strain FRD1 grew more slowly than non-mucoid PAO1 and FRD1/pmucA. Strain FRD1 was selected because it is the best characterized mucoid, mucA22 mutant CF isolate (Goldberg J B, and Ohman D E. 1984. J. Bacteriol. 158:1115-1121), and has recently been sequenced. However, no difference in viability patterns was observed (FIG. 1A). Using 15 mM A-$NO_2^-$ (that is non-toxic to non-mucoid bacteria) mucoid FRD1 was killed at a rate of ~90% per day, while two non-mucoid strains, PAO1 and FRD1/pmucA, remained viable over the 4 day incubation (FIG. 1B). After discovering this unique A-$NO_2^-$ sensitivity of mucA mutant strain FRD1, we also found that $NO_2^-$ killed these bacteria more effectively at lower pH while little or no killing was observed in the mucA complemented strain, FRD1/pmucA, at pH values between 6.0 and 7.5 (FIG. 1C). To explore the potential clinical application of A-$NO_2^-$ in the treatment of mucoid PA infections in chronic CF/COPD patients, we first tested the effect of A-$NO_2^-$ on the viability of biofilm bacteria. Anaerobic biofilms of strains FRD1 and FRD1/pmucA were grown for 1 day in LB-$NO_3^-$, which supports anaerobic growth. Since mucoid strain FRD1 lacks a flagellum (Garrett E S, et al. 1999. J Bacteriol 181:7401-7404), a surface appendage that is critical for PA biofilm initiation (O'Toole G A, Kolter R. 1998 Mol Microbiol 30:295-304), strain FRD1 formed much weaker biofilms compared to those of flagellated FRD1/pmucA (FIG. 1 D,E). When the FRD1 biofilm was treated with $NO_2^-$ at pH 7.5 for 2 days, no difference in biofilm structure and cell viability (live cells are green, red cells are dead) was observed relative to control biofilms. In contrast, nearly complete death of biofilm bacteria was observed at pH 6.5. We then determined the efficacy of A-$NO_2$ to kill strain FRD1 in a PA chronic lung infection model. Currently, there is no animal model for the anaerobic biofilm mode of CF/COPD airway disease or animals that acquires spontaneous PA infections. However, CD1 mice, inoculated with agarose beads impregnated with bacteria, have been useful for studying chronic lung infection by PA (Lau G W, et al. 2004. Infect Immun 72:4275-4278).

Anaerobic growth of PA strains at pH 6.5 using 15 mM $NO_3^-$ or $NO_2^-$ as a terminal electron acceptor. Diluted suspensions of PAO1, FRD1 or FRD1/pmucA were incubated anaerobically with NO3$^-$ (FIG. 1A) or NO2$^-$ (FIG. 1B). (FIG. 1C) NO2$^-$ sensitivity vs. pH. FRD1 or FRD1/pmucA were seeded onto LB agar buffered at the indicated pH value. After placing a filter disk containing 10 μl of 1 M $NO_2^-$, the plates were incubated anaerobically for 48 hr. (FIG. 1D) Confocal laser microscopic analysis of anaerobic FRD1 biofilms. Live cells are green, red cells are dead. Before staining, 1-day old anaerobic FRD1 biofilms were treated anaerobically with 15 mM $NO_2^-$ at pH 6.5 (top right) and 7.5 (bottom right) for 2 d. (FIG. 1E) Biofilms were grown as above in panel A except using FRD1/pmucA. (FIG. 1F) Effects of $NO_2^-$ on killing of FRD1 and FRD1/pmucA in mouse lungs. Infected mice were treated with buffer (black bars) and buffered $NO_2^-$ (hatched bars) daily and viable bacteria from the lung homogenates were enumerated. (FIG. 1G) Effects of long-term (16 d) 15 mM $NO_2^-$ treatment on killing of FRD1 in mouse lungs days. Eight mice were used for each treatment and significance was *p<0.01. (FIG. 1H) Competitive index experiments with $10^6$ FRD1 and FRD1 (pmucA) intratracheally instilled into CD1 mouse airways and incubated for 6 days prior to harvesting of mouse lungs and enumeration of CFU after homogenization.

Consistent with in vitro results, mucoid FRD1, but not non-mucoid FRD1/pmucA, were decreased >2 logs at pH 6.5 and >3 logs at pH 5.5 by $HNO_2^-$ in vivo (FIG. 1F). Because NO concentrations derived from A-$NO_2^-$ are 10-fold greater with a reduction of 1 pH unit, these results are consistent with classical $NO_2^-$ reduction chemistry. Furthermore, organisms that were recovered from the mouse airways after $NO_2^-$ exposure were still sensitive to $NO_2^-$ in vitro, although these results do not clearly indicate that NO itself within the bacterial cytoplasm is the toxic species. Long-term treatment with $HNO_2$ was also addressed and produced progressively decreasing airway titers of mucoid, mucA mutant bacteria $NO_2^-$ was instilled on a daily basis in mice infected with mucoid organisms for a period of 16 days. FIG. 1G shows that there were no bacteria detected in mice treated for 16 days with $HNO_2^-$, while buffer control mice still harbored nearly $10^4$ mucoid organisms per lung. To address the possibility that acidified A-$NO_2^-$ can kill mucoid mucA mutant bacteria in the presence of non-mucoid bacteria in vivo, competitive index experiments were performed. FIG. 1H demonstrates that the competitive index was only ~0.2 for mucoid, mucA mutant strain FRD1 relative to its complemented strain, FRD1/pmucA, which was ~1.0.

Example 2: A-$NO_2^-$, EDTA and Tobramycin Act Synergistically as a Powerful Bactericidal Combination Against *P. Aeruginosa*

A major byproduct of A-$NO_2^-$ that poisons PA is the production of nitric oxide (NO). PA has anaerobic enzymatic machinery in the form of NO reductase which is critical for optimal defense against metabolically generated NO as well as A-$NO_2^-$ provided exogenously (Yoon S S, et al. 2006. J. Clin. Invest. 116:436-446; Yoon S S, et al. 2007. Embo J 26:3662-3672). NO compromises the function of intracellular iron/heme containing proteins (Su S, et al. 2014. PLoS One 9:e91813) in PA. It is hypothesized that using A-$NO_2^-$ coupled with an iron chelator such as EDTA (ethylenediaminetetraacetic acid), thereby not only compromising bacterial membranes (Eagon R G, Carson K J. 1965. Can J Microbiol 11:193-201) but chelating extracellular iron, that bacteria would be killed even more effectively. EDTA alone has been previously shown to not modify the clinical course or the airway microbial flora in CF patients chronically infected with PA (Brown J, et al. 1985. Am J Dis Child 139:836-839).

FIG. 2 represent optical density measurements with control (untreated) bacteria arbitrarily set to 1.0 after 24 and 48 hr of growth at 37° C. in a standard rich medium known Luria broth (LB). Another experiment included the powerful aminoglycoside antibiotic, tobramycin (TOBI), that is commonly used for the treatment of PA CF/COPD lung infections (Moreau-Marquis S, et al. 2009. Am J Respir Cell Mol Biol 41:305-313; Dal Negro R, et al. 2008. Adv Ther 25:1019-1030). Nitrite was used at 25 mM (aerobic) or 15 mM (anaerobic); EDTA, 1.0 mM; TOBI, 2 μg/ml. Anaerobic LB was supplemented with 0.1 M potassium phosphate, pH 6.5 and 100 mM $KNO_3$ as a terminal electron acceptor for anaerobic growth.

Furthermore, these results show that growth of the common non-mucoid laboratory strain known as PAO1 is initially impaired by 15 mM A-$NO_2^-$ or 1 mM EDTA and 2 μg/ml TOBI. Unlike aerobic conditions where the antimicrobial activity of aminoglycosides is highly effective, TOBI was not effective at killing PA under anaerobic conditions. Note, however, that the combination of A-$NO_2^-$-EDTA-TOBI was effective at killing all bacteria under both aerobic and anaerobic conditions. It should be mentioned here that these very low concentrations of A-$NO_2^-$-EDTA-TOBI do not harm airway epithelial cells. In fact, if needed, far higher concentrations of A-$NO_2^-$-EDTA-TOBI could be used without harmful effects to the host.

Example 3: Assessing Sensitivity of Microorganisms to Acidified Nitrite and EDTA The study of interactive effects between molecules has a long history. The value of the FIC index as a predictor of synergy has been investigated using the antibacterial agents alafosfalin and cephalexin combined together with themselves in fully blind experiments. Under the conditions used, even weak interaction (FIC index 0.5-0.99) proved to be statistically highly significant The use of such fully controlled blind studies would greatly enhance the credibility of many of the claims of synergy published in the literature. The representation of results as average isobolograms is only of value with combinations which show moderate to strong interaction. (Hall et al., J. Antimicrob. Chemother. (1983) 11 (5):427-433.)

Checkerboard Assay

For antimicrobial drugs, the use of paired and triple combinations of inhibitory agents in the clinic often begins with tests in vitro that show positive interactions inhibiting the growth of target microorganisms. There are many models for experimental designs to measure such combination effects. One of the best known and very simple forms of such tests is the 'checkerboard' experiment. This method uses a two-dimensional array of serial concentrations of test compounds is used as the basis for calculation of a fractional inhibitory concentration index (FICI) to demonstrate that paired combinations of agents can exert inhibitory effects that are more than the sum of their effects alone (synergy; FICI<1.0), or less than the sum of their effects alone (antagonism; FICI>1.0). Certain journals have adopted certain FICI ranges to define 'synergy' (FICI≤0.5), 'antagonism' (FICI>4.0) and 'no interaction' (FICI>0.5-4.0) to encourage conservative interpretation of results in the antimicrobial field. (Odds, F. C., J. Antimicrob. Chemother., (2003 52(1):1.)

In these assays, bacteria are layered of top of the wells at ~$10^5$ CFU/ml. Aerobic samples are incubated for 24 hours, and anaerobic samples are incubated for 48 hours. FICI is determined by adding the fraction of individual minimum inhibitory concentrations (MICs) together.

The following bacteria were assayed with this method. *P. aeruginosa, E. coli, K. pneumoniae, S. maltophila, A. baumannii, P. mirabilis, B. cepacia, S. typhimurium, E. cloacae, H. pylori, S. aureus, S. epidermidis, B. anthracis, E. faecalis, S. pyrogenes, L. monocytogenes, Stretomyces* spp., *Nocardia* spp., *Corynebacterium*, and *M. smegmatis*.

Results

Most strains reported showed useful data. Some strains (*B. anthracis, L. monocytogenes*) were attempted, but media growth requires additional optimization.

FIG. 3 provides checkerboard assay MIC and associated FIC scores for *P. aeruginosa* for aerobic (3A) and anaerobic (3B) conditions.

Figure 4A:
FIG. 4 provides checkerboard assay MIC and associated FIC scores for *E. coli* for aerobic (FIG. 4A) and anaerobic (FIG. 4B) conditions.
Figure 4B:
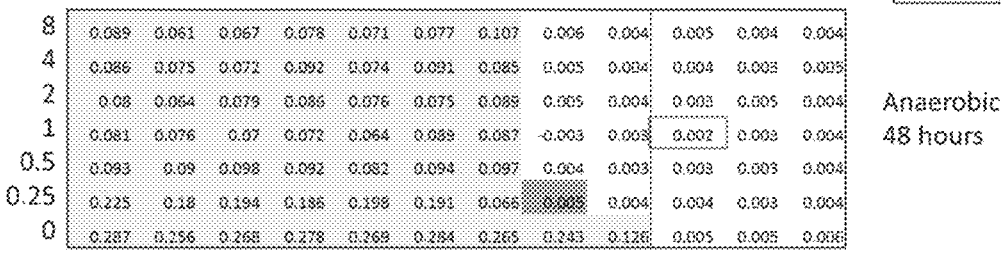

FIG. 4 provides checkerboard assay MIC and associated FIC scores for *E. coli* for aerobic (4A) and anaerobic (4B) conditions.

Figure 5A:
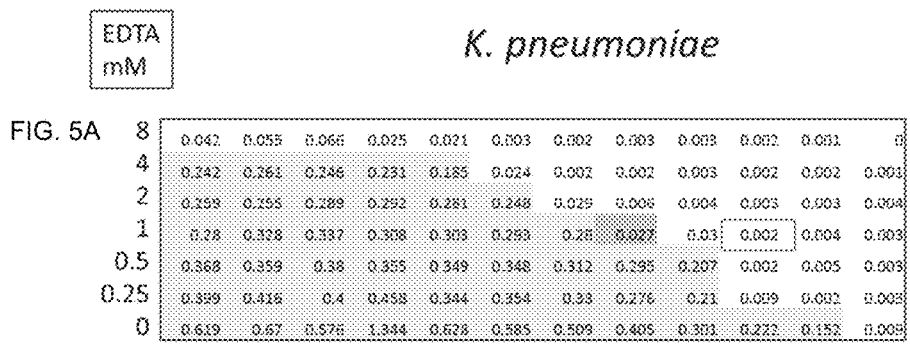
FIG. 5 provides checkerboard assay MIC and associated FIC scores for *K. pneumoniae* for aerobic (FIG. 5A) and anaerobic (FIG. 5B) conditions.
Figure 5B:
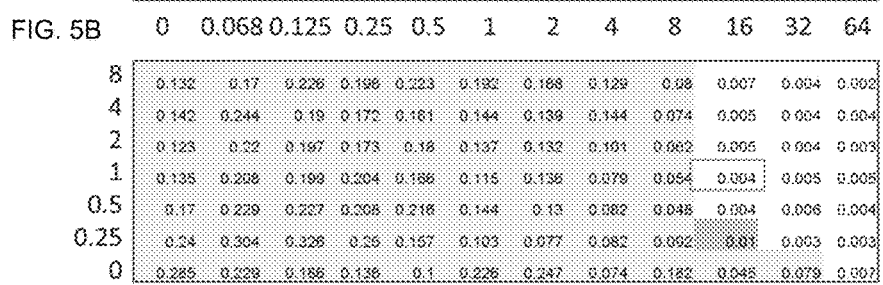

FIG. 5 provides checkerboard assay MIC and associated FIC scores for *K. pneumoniae* for aerobic (5A) and anaerobic (5B) conditions.

FIG. 6 provides checkerboard assay MIC and associated FIC scores for *S. aureus* for aerobic (6A) and anaerobic (6B) conditions.

FIG. 7 provides checkerboard assay MIC and associated FIC scores for *S. typhimirium* for aerobic (7A) and anaerobic (7B) conditions.

FIG. 8 provides checkerboard assay MIC and associated FIC scores for *P. mirabilis* for aerobic (8A) and anaerobic (8B) conditions.

FIG. 9 provides checkerboard assay MIC and associated FIC scores for *Corynebacterium* spp. for aerobic (9A) and anaerobic (9B) conditions.

FIG. 10 provides checkerboard assay MIC and associated FIC scores for *A. baumannii* for aerobic conditions.

FIG. 11 provides checkerboard assay MIC and associated FIC scores for *E. cloacae* for aerobic (11A) and anaerobic (11B) conditions.

FIG. 12 provides checkerboard assay MIC and associated FIC scores for *E. faecalis* for aerobic (12A) and anaerobic (12B) conditions.

FIG. 13 provides checkerboard assay MIC and associated FIC scores for *S. epidermidis* for aerobic (13A) and anaerobic (13B) conditions.

Figure 14:
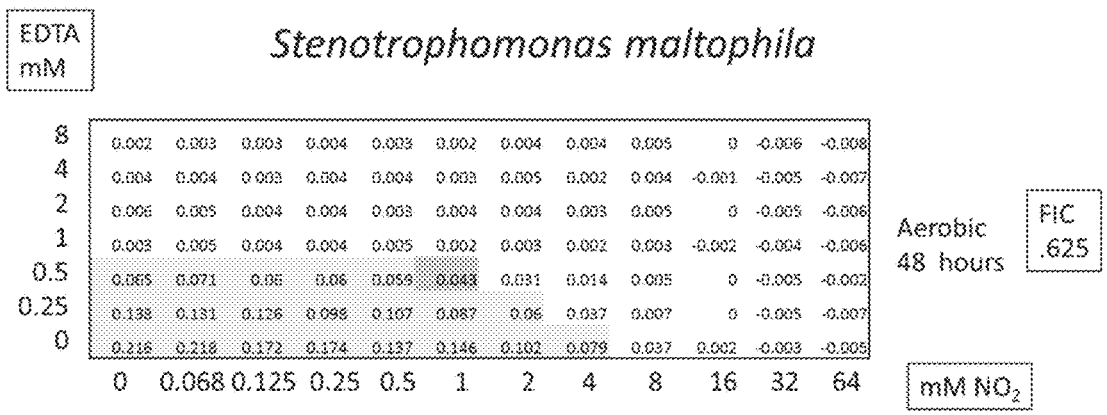
FIG. 14 provides checkerboard assay MIC and associated FIC scores for *S. maltophila* for aerobic conditions.

FIG. 14 provides checkerboard assay MIC and associated FIC scores for *S. maltophila* for aerobic conditions.

Figure 15:
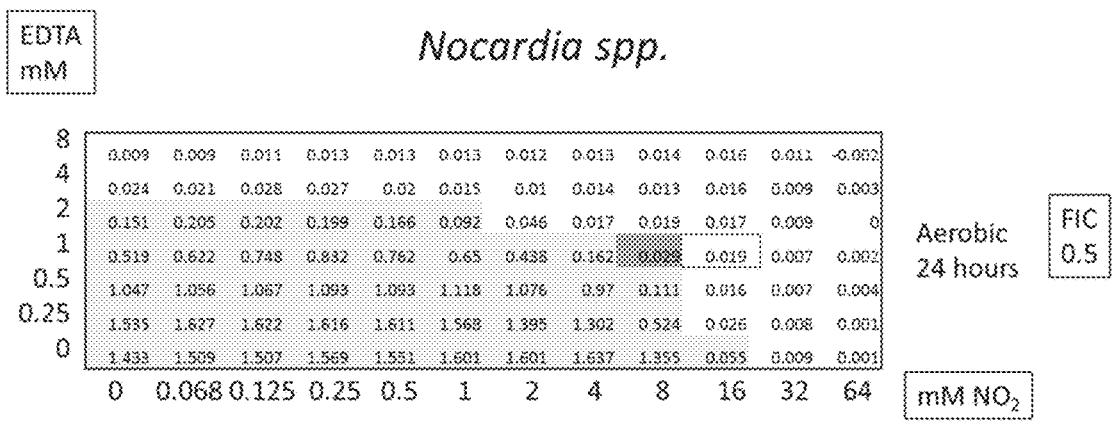
FIG. 15 provides checkerboard assay MIC and associated FIC scores for *Nocardia* spp. for aerobic conditions.
Figure 27A:
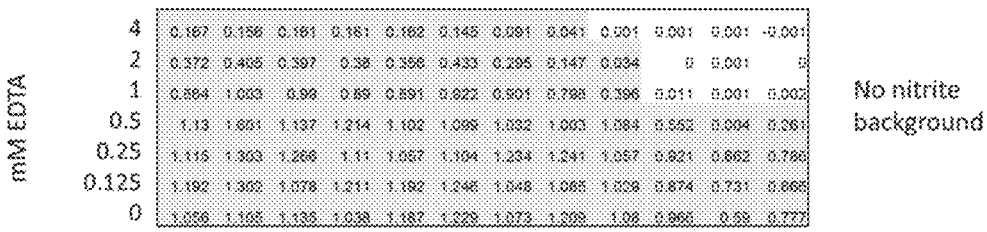
FIG. 27 provides checkerboard assay MIC and associated FIC scores for vancomycin for aerobic (FIG. 27A and FIG. 27B) and anaerobic (FIG. 27C and FIG. 27D) conditions with and without a nitrite background (7.5 mM).
Figure 27B:
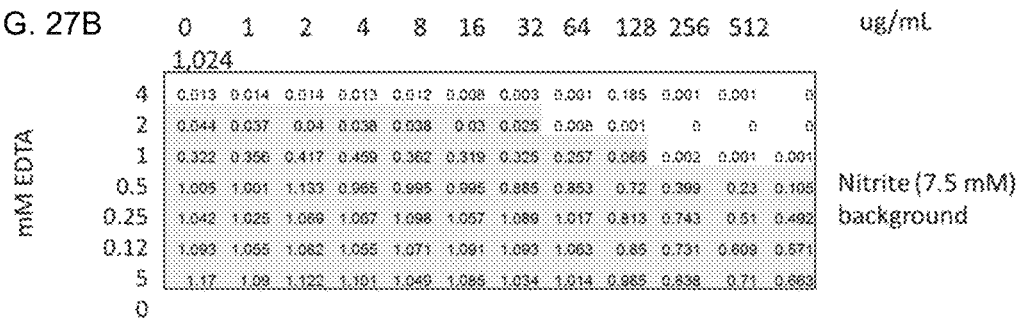
Figure 27C:
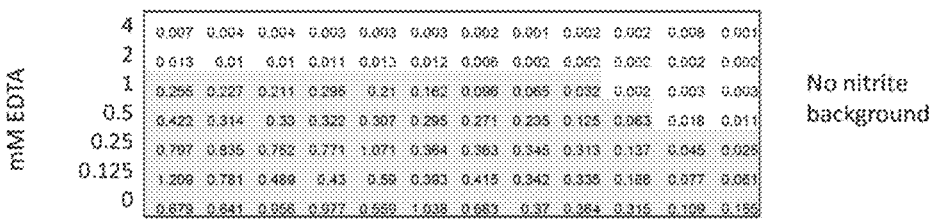
Figure 27D:
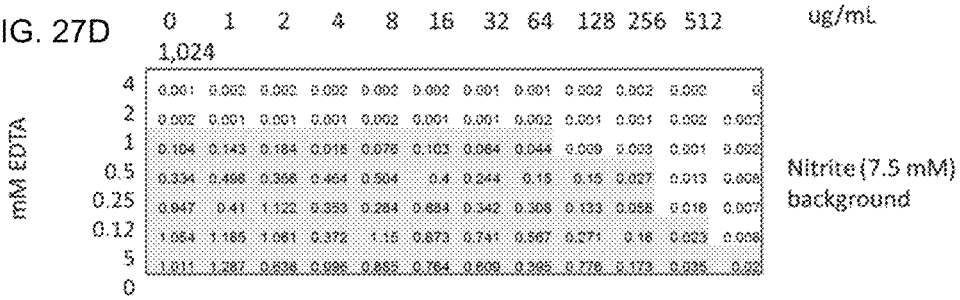
Figure 28A:
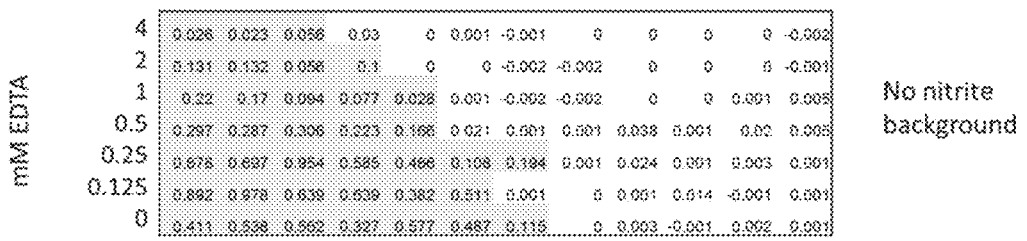
FIG. 28 provides checkerboard assay MIC and associated FIC scores for cefepime for aerobic (FIG. 28A and FIG. 28B) and anaerobic (FIG. 28C and FIG. 28D) conditions with and without a nitrite background (7.5 mM).
Figure 28B:
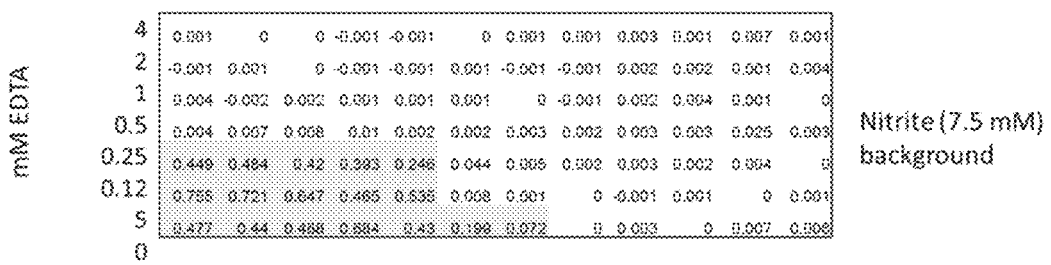
Figure 28C:
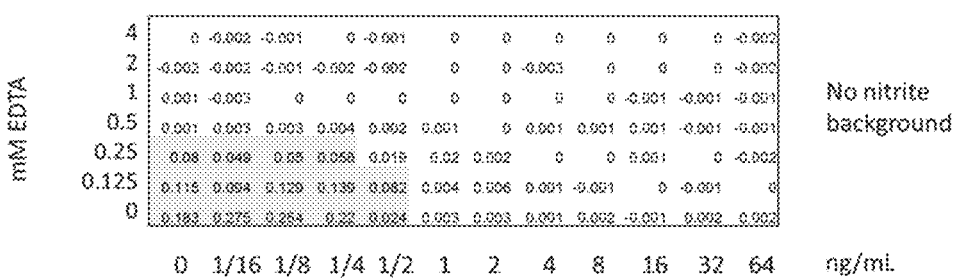
Figure 28D:
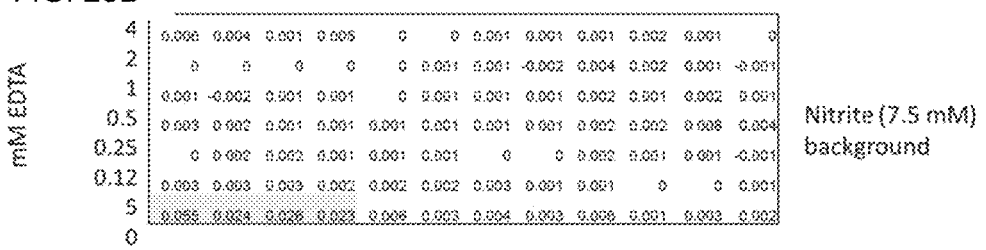
Figure 30A:
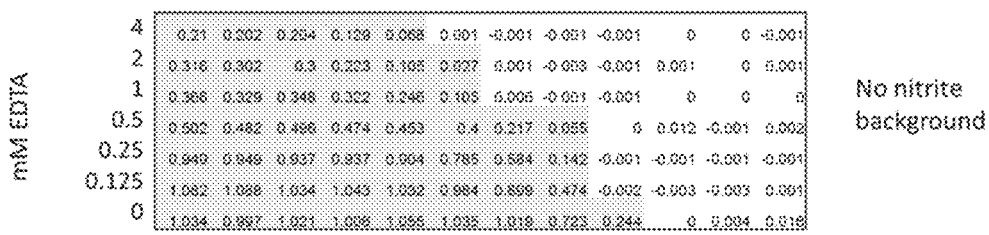
FIG. 30 provides checkerboard assay MIC and associated FIC scores for tetracycline for aerobic (FIG. 30A and FIG. 30B) and anaerobic (FIG. 30C and FIG. 30D) conditions with and without a nitrite background (7.5 mM).
Figure 30B:
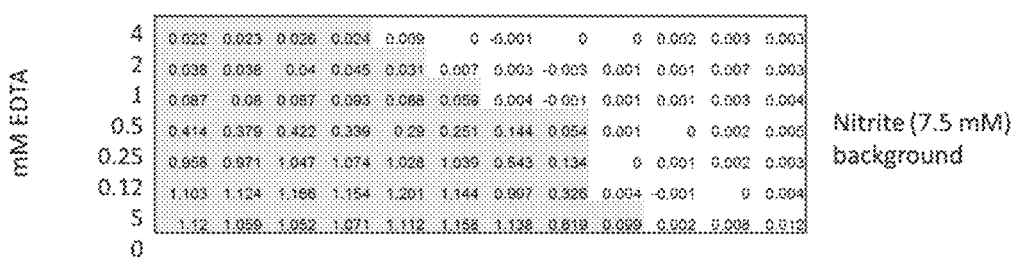
Figure 30C:
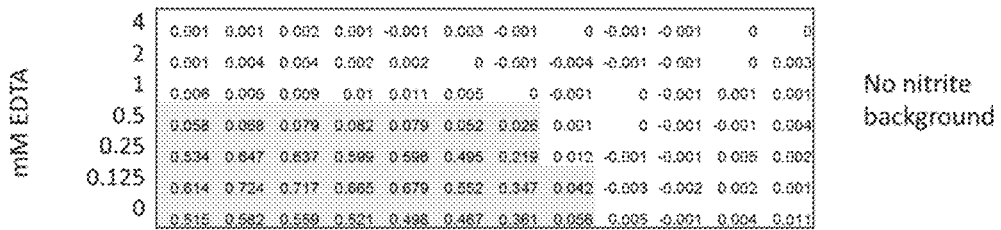
Figure 30D:
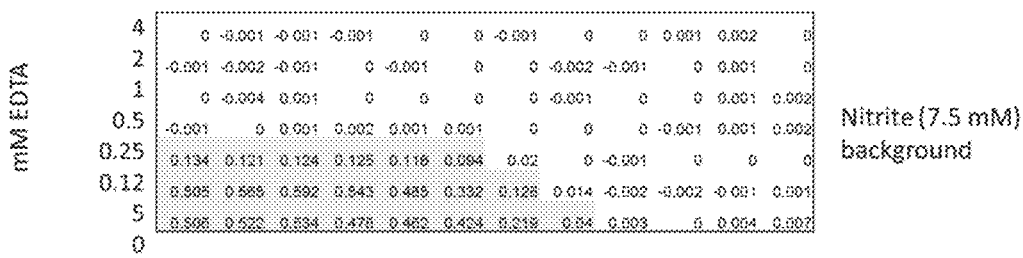

FIG. 15 provides checkerboard assay MIC and associated FIC scores for *Nocardia* spp. for aerobic conditions.

FIG. 16 provides checkerboard assay MIC and associated FIC scores for *S. pyrogenes* for aerobic (16A) and anaerobic (16B) conditions.

FIG. 17 provides checkerboard assay MIC and associated FIC scores for *M. smegmatis* for aerobic conditions.

The results of the FIC study summarizing synergy are provided in FIG. 18. The concentrations at FIC relevant to current treatment concentrations are provided in FIG. 19.

Example 4: Triple Sensitivities of A-NO$_2$, EDTA and Antibiotic Agents on Cultures of *P. Aeruginosa*

To assess triple sensitivities of the combination of A-NO$_2$, EDTA and various antibiotic agents. A checkerboard assay was used to assess the synergy between EDTA and antibiotics in the presence and absence of an acidified nitrite background.

The antibiotic agents used in these studies included Tobramycin, Azithromycin, Colistin, Ticarcillin, Ciprofloxacin, Sulfametoxazole, Sulfamethazine, Tetracycline, Vancomycin, Imipenem, and Cefepime.

In these assays, bacteria are layered of top of the wells at ~$10^5$ CFU/ml. Aerobic samples are incubated for 24 or 48 hours, and anaerobic samples are incubated for 48 hours.

Results

As expected, all MICs of EDTA decreased upon addition of acidified nitrite.

FIG. 20 provides checkerboard assay MIC and associated FIC scores for tobramycin for aerobic (FIG. 20A and FIG. 20B) and anaerobic (FIG. 20C and FIG. 20D) conditions with and without a nitrite background (7.5 mM).

FIG. 21 provides checkerboard assay MIC and associated FIC scores for ciprofloxacin for aerobic (FIG. 21A and FIG. 21B) and anaerobic (FIG. 21C and FIG. 21D) conditions with and without a nitrite background (7.5 mM).

FIG. 22 provides checkerboard assay MIC and associated FIC scores for ticarcillin for aerobic (FIG. 22A and FIG. 22B) and anaerobic (FIG. 22C and FIG. 22D) conditions with and without a nitrite background (7.5 mM).

FIG. 23 provides checkerboard assay MIC and associated FIC scores for colistin for aerobic (FIG. 23A and FIG. 23B) and anaerobic (FIG. 23C and FIG. 23D) conditions with and without a nitrite background (7.5 mM).

FIG. 24 provides checkerboard assay MIC and associated FIC scores for azithromycin for aerobic (FIG. 24A and FIG. 24B) and anaerobic (FIG. 24C and FIG. 24D) conditions with and without a nitrite background (7.5 mM).

FIG. 25 provides checkerboard assay MIC and associated FIC scores for sulfamethazine for aerobic (FIG. 25A and FIG. 25B) and anaerobic (FIG. 25C and FIG. 25D) conditions with and without a nitrite background (7.5 mM).

FIG. 26 provides checkerboard assay MIC and associated FIC scores for sulfamethoxazole for aerobic (FIG. 26A and FIG. 26B) and anaerobic (FIG. 26C and FIG. 26D) conditions with and without a nitrite background (7.5 mM).

FIG. 27 provides checkerboard assay MIC and associated FIC scores for vancomycin for aerobic (FIG. 27A and FIG. 27B) and anaerobic (FIG. 27C and FIG. 27D) conditions with and without a nitrite background (7.5 mM).

FIG. 28 provides checkerboard assay MIC and associated FIC scores for cefepime for aerobic (FIG. 28A and FIG. 28B) and anaerobic (FIG. 28C and FIG. 28D) conditions with and without a nitrite background (7.5 mM).

FIG. 29 provides checkerboard assay MIC and associated FIC scores for imipenem for aerobic (FIG. 29A and FIG. 29B) and anaerobic (FIG. 29C and FIG. 29D) conditions with and without a nitrite background (7.5 mM).

FIG. 30 provides checkerboard assay MIC and associated FIC scores for tetracycline for aerobic (FIG. 30A and FIG. 30B) and anaerobic (FIG. 30C and FIG. 30D) conditions with and without a nitrite background (7.5 mM).

Azithromycin shows best results so far in combination, possibly due to effects as secondary chelator.

Certain species show greater sensitivity to EDTA/$NO_2^-$ than others, but antagonism is not seen. The combination helps reduce the overall thickness of the biofilms.

Example 5: Artificial Urine Media (AUM) and Volunteer Urine Analysis

To determine the efficacy of the combination treatment in urine, we inoculated both an artificial standard urine and 5 volunteer urine samples with 5 strains of bacteria associated with UTIs, and applied the same checkerboard method to determine the efficacy of the treatment.

For urine sampling, all volunteers asked to volunteer urine samples from 1st evacuation in the morning. Samples filter sterilized before use. All volunteers are Age 22-26, Male. For the human studies, male volunteers (age 22-26) sterilized the glans penis prior to voiding in the morning with 70% ethanol. The volunteer was then allowed to urinate ~5 ml and the remainder collected in sterile urine. The pH of human urine in the morning is ideal for the antimicrobial effects of acidified nitrite.

The bacteria used for this study included *P. aeruginosa* (PAO1), *E. coli* (clinical UTI derivative strain), *S. aureus* (USA300), *K. pneumoniae*, *Staphylococcus saprophyticus* (clinical strain Known UTI associated pathogen)

All studies carried out aerobically at 37° C., static growth in polystyrene 96-well plates at pH 5.5 and pH 6.5.

Results

Volunteer Urine showed that the treatment is effective against bacteria in actual human urine and supports further study in a mouse model of UTI.

AUM testing shows that with a pH close to 6.5, the treatment was far less effective than at 5.5. However, all morning samples from volunteers were less than pH 6.0.

FIG. 31 provides a summary of the FIC values showing synergy for the artificial urine media and the volunteer urine samples.

Combination testing in Urine/Artificial Urine suggests that it is effective, but at a lower pH.

Example 6: In Vivo Efficacy in a Mouse Model of Chronic Respiratory Infection

This model recapitulates the mucoid environment produced by a chronic infection.

BALB/c mice (8 per group) were infected with $1.7 \times 10^6$ *P. aeruginosa* (PAO1) in 1 mg/ml alginate. To account for bacteria in alginate (similar to biofilm), dose of each compound was increased based on previous biofilm data.

A combination composition of a molar ratio of $NaNO_2$ and EDTA (range $NaNO_2$:EDTA-1:1 to 3:1) in aqueous solution is administered as an inhaled (nebulized) therapy. NaNO2 (15 mM) at pH of <7.0 (typical of the airway mucus in cystic fibrosis patients that have a pH of ~6.5) dissociates to acidified nitrite (A-$NO^{2-}$) which in turn generates ~490 nM nitric oxide (NO).

The infected mice (n=8) were treated with either (i) 10 mM PBS, pH 6.5, (ii) 10 mM EDTA in PBS, pH 6.5, (iii) 30 mM $NaNO_2$ in PBS, pH 6.5, or (iv) 10 mM EDTA-10 mM $NaNO_2$ in PBS, pH 6.5. Agents were administered as inhaled therapies beginning at 12 hours post-inoculation and continued once daily. EDTA/$NaNO_2$ reduced the pulmonary burden of *P. aeruginosa* PAO1 by almost 2 logs compared to control mice. EDTA/$NaNO_2$ was also more effective than either agent alone. Data are analyzed using a one-way ANOVA with a Tukey post-hoc test and are highly significant with $p<0.001$.

Results

Figure 32:
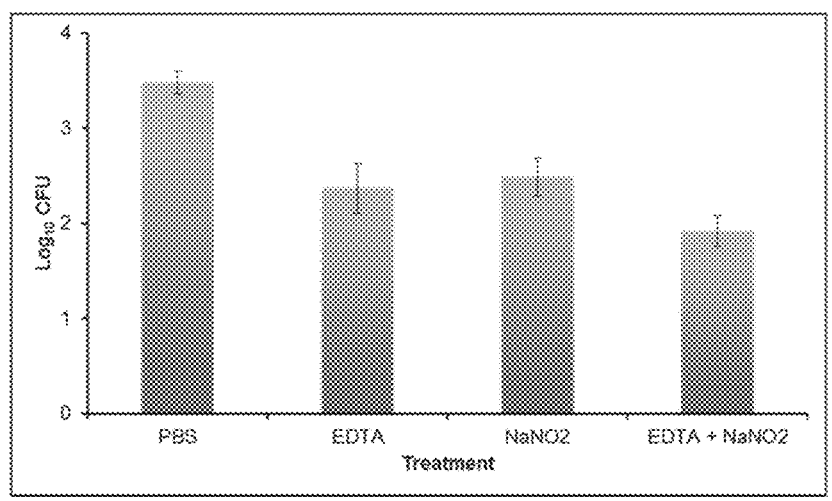
FIG. 32 provides a graph showing the average CFU/lung is reduced by NO$_2$ and EDTA alone and in combination relative to control (PBS).

There is a dramatic synergistic reduction in viable *P. aeruginosa* titers when EDTA is combined with $NaNO_2$. In addition, the combination of $NaNO_2$ and EDTA also shows synergy against other major CF pathogens including *K. pneumonia*, *A. baumannii* and *S. maltophilia*. Importantly, this combination synergistically increases the bactericidal activity of tobramycin and especially azithromycin, two antibacterial agents that are routinely the standard of care for CF lung infections Average CFU/lung is reduced by $NO_2$ and EDTA alone and in combination relative to control (PBS) as shown in FIG. 32.

The combination of $NO_2$ and EDTA resulted in a 2-log reduction in the pulmonary burden of *P. aeruginosa* compared to control mice. The mouse models used in the above studies are best representative of *P. aeruginosa* pulmonary infection in vivo since animal models that truly mimic CF lung infections in humans are not available.

Summary

The combination of active ingredients $NaNO_2$ and EDTA, demonstrates potent in vitro and in vivo inhibition of *P. aeruginosa* and other bacteria that cause chronic lung infections in CF patients. $NaNO_2$ and EDTA separately have been evaluated in humans in a number of different contexts and shown to have minimal toxicity. Therefore, this combination represents a potentially effective agent, to be used as monotherapy or in conjunction with standard of care to control mucoid and non-mucoid *P. aeruginosa* (and potentially other organisms) pulmonary infections in patients with CF.

Example 7: Assessing Effect of $NO_2$ and EDTA on Elimination of Pre-Existing Biofilm In order to determine the efficacy of the combination treatment for biofilm elimination, we employed a Crystal Violet assay. This allows us to determine the total biomass of the biofilm.

Crystal Violet stains biofilm mass which is a quantitative measure of biofilm density/thickness, but not necessarily viability (live/dead) of the biomass.

Cultures are grown for 24 hours aerobically or anaerobically, and then treated for 24 hours before assay.

*P. aeruginosa* was allowed to adhere to 96 well polystyrene 96 well microplates at incubate at 37° C. under aerobic vs. anaerobic conditions. The biofilms were washed with PBS and stained with 1% crystal violet (CV) for 15 minutes at room temperature. The CV was removed and the stained bacteria washed an additional 3 times prior to solubilization of the CV with 95% ethanol. The absorbance at 590 nm was monitored using a microplate reader.

Results

Figure 33A:
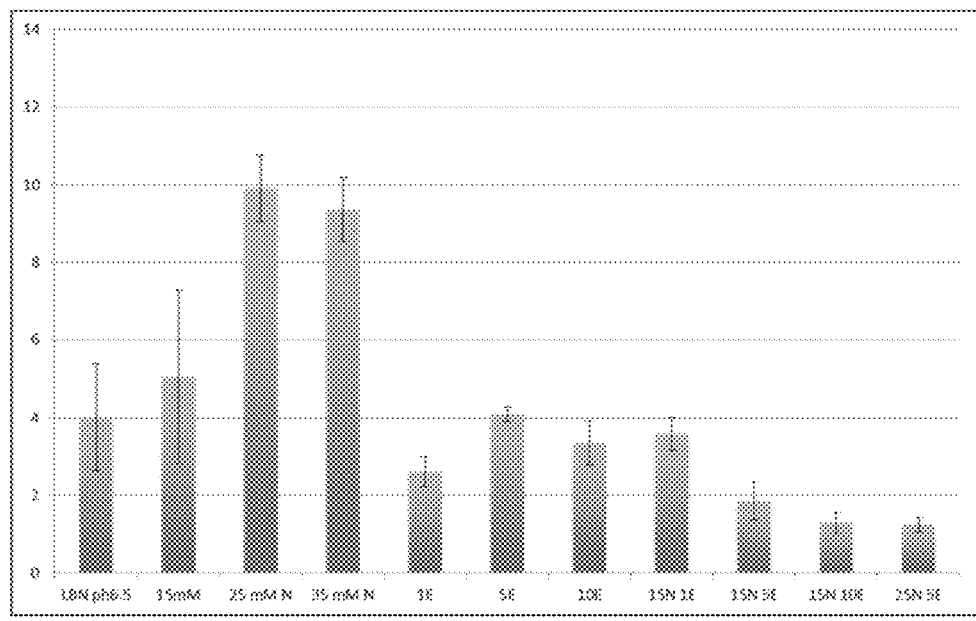
FIG. 33A and FIG. 33B provide graphs showing the results of acidified nitrite (15 mM, 25 mM, and 35 mM) and EDTA (1 mM, 5 mM, and 10 mM) alone and in combination for aerobic conditions (FIG. 33A) and for anaerobic conditions (FIG. 33B).
Figure 33B:
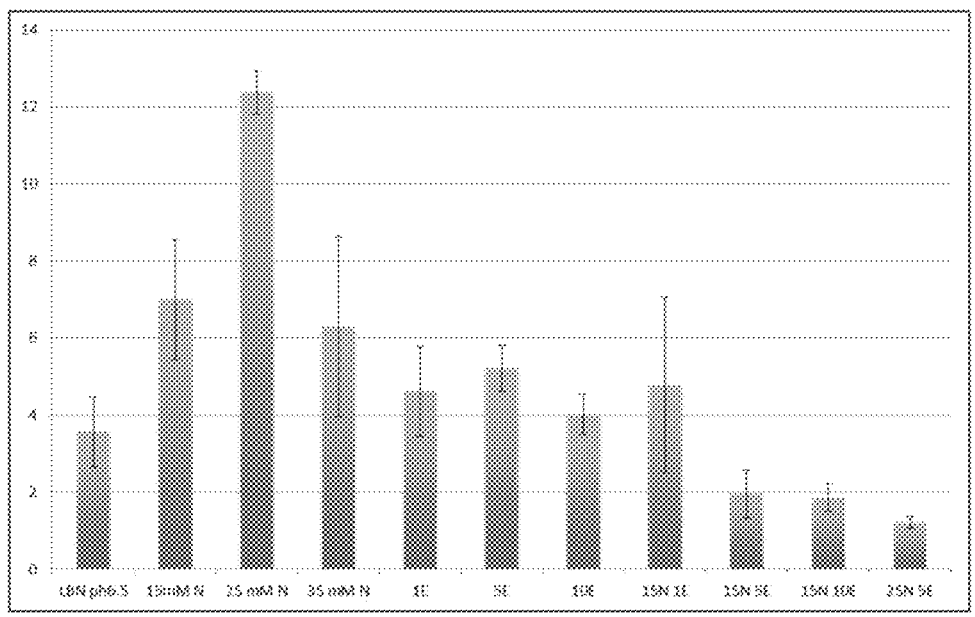

The results of acidified nitrite (15 mM, 25 mM, and 35 mM) and EDTA (1 mM, 5 mM, and 10 mM) alone and in combination are provided in FIG. 33A for aerobic conditions and FIG. 33B for anaerobic conditions and demonstrate reduction of biomass density/thickness with the most pronounced effect with 15 mM A-$NO_2$ and 5 mM EDTA. LBN pH 6.5 control is also provided.

Figure 34A:
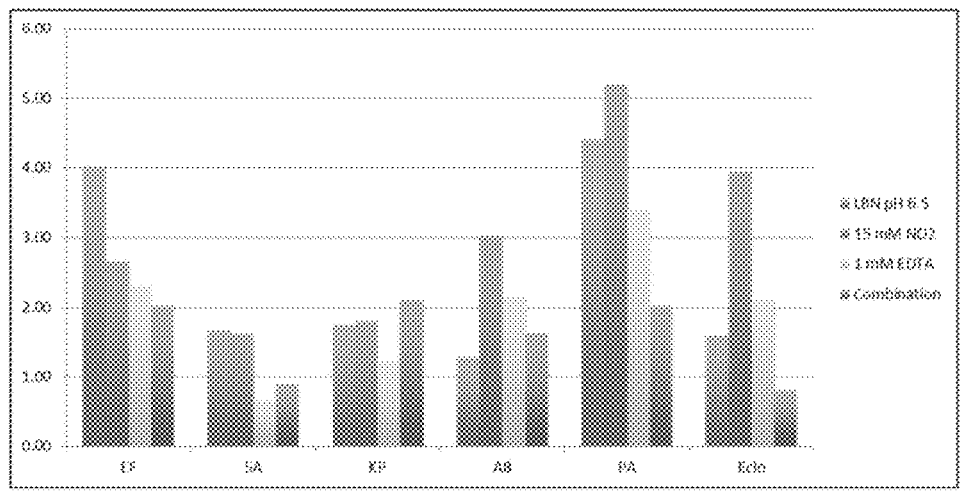
FIG. 34A and FIG. 34B provide graphs showing the effect of acidified nitrite (15 mM) and EDTA (1 mM) alone and in combination for aerobic conditions (FIG. 34A) and for anaerobic conditions (FIG. 346) for various bacteria on pre-existing biofilms. (EF=*E. faecalis*, SA=*S. aureus*, KP=*K. pneumoniae*, AB=*A. baumanii*, PA=*P. aeruginosa*, and Eclo=*E. cloacae*) and demonstrate reduction of biomass density/thickness with the most pronounced effect resulting from the combination of 15 mM A-NO$_2$ and 1 mM EDTA. LBN pH 6.5 control is also provided. The net O.D. (y-axis) decrease is an indicator of effectiveness of nitrite, EDTA or both
Figure 34B:
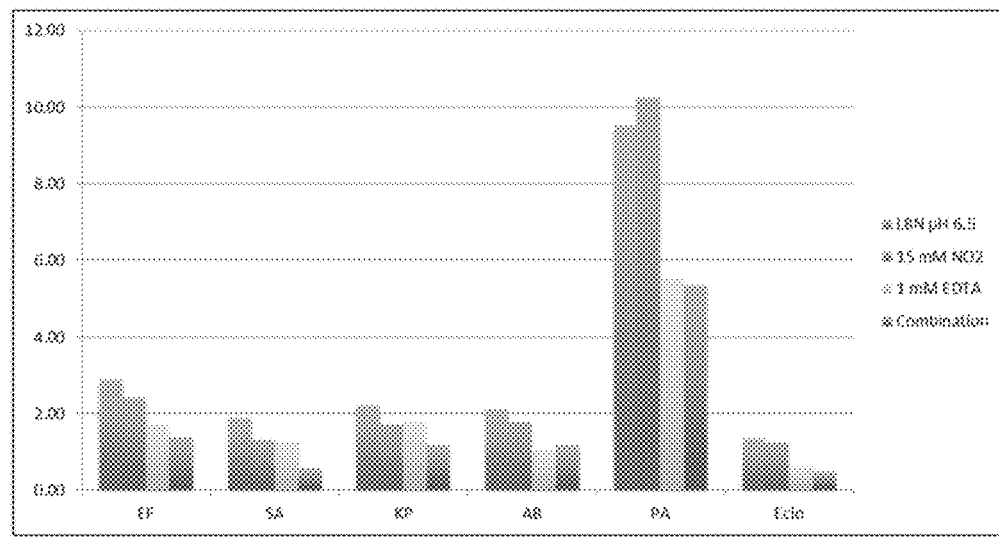

The results of acidified nitrite (15 mM) and EDTA (1 mM) alone and in combination are provided in FIG. 34A for aerobic conditions and FIG. 34B for anaerobic conditions for various bacteria. (EF=*E. faecalis*, SA=*S. aureus*, KP=*K. pneumoniae*, AB=*A. baumannii*, PA=*P. aeruginosa*, and Eclo=*E. cloacae*) and demonstrate reduction of biomass density/thickness with the most pronounced effect resulting from the combination of 15 mM A-$NO_2$ and 1 mM EDTA. LBN pH 6.5 control is also provided.

Example 8: Metal Competition Assay to Assess Metal Binding on Efficacy

The purpose of this study was to test which metals may be important in this treatment, we treated cells with 15 mM $NaNO_2$, 1 mM EDTA, or a combination of $NaNO_2$/EDTA along with 1 mM of a metal solution. Bacterial cultures were incubated under anaerobic conditions for 24 and 48 hours.

TABLE 1

Stability Constant for EDTA-Metal Complexes

| Metal Ion | Stability Constant |
|---|---|
| Barium | 7.78 |
| Strontium | 8.63 |
| Magnesium | 8.69 |
| Calcium | 10.70 |
| Manganese | 13.56 |
| Iron (II) | 14.3 |
| Aluminum (III) | 16.13 |
| Cobalt (II) | 16.21 |
| Zinc (II) | 16.5 |
| Nickel | 18.56 |
| Copper | 18.8 |
| Mercury | 21.5 |
| Iron (III) | 25.7 |

The greater the stability constant, the more likely it is EDTA will preferentially bind a particular metal in comparison to other metals. Barium, Magnesium, Calcium, Iron (II), and Zinc (II) were found to be significant. Magnesium is critical for LPS structure as well as ATP synthesis and utilization. Calcium is a cofactor for many enzymes and is also a part of the gram-negative LPS layer. Iron is critical for bacterial life, synthesis of heme, cytochromes and antioxidants. It also significantly binds NO, a by-products of A-$NO_2^-$.

Nitric Oxide Analysis Via High Sensitivity Probe

ISO-NOP Studies were conducted using a sensitive probe to detect miniscule changes in NO levels and recorded as electrical current (pA).

After addition of $NO_2$ the production of NO in the system is measured.

Studies were conducted using a glass vessel shaped much like a "pig", connected to a circulating water supply to maintain temperature.

First LBN pH 6.5 studies are conducted using the normal media to determine if there is a change in the NO production based on the treatment.

Results

First, baseline tracings were established to ensure proper functioning of the World Precision Instruments NO electrode. 15 mM A-$NO^{2-}$ was freshly prepared and added to the electrode system as previously described in 2006 by Yoon et al., {Yoon, 2006 #3174}. After ~27 hr, there was ~473 nM NO generated in the system. This is similar to the 490 nM NO generated in the Yoon et al., {Yoon, 2006 #3174} paper confirming proper functioning of the electrode.

Effect of EDTA on the doubling of NO production in our NO electrode studies. 1 mM EDTA (disodium form) was added and measured using the electrode showing that the combination of $NO_2$ and EDTA creates 2× as much NO than $NO_2$ alone in LBN pH 6.5.

Use of a minimal buffer system. Due to potential confounding factors in LBN, we turned to PBS, pH 6.5.

To evaluate whether EDTA needs to chelate a particular metal (or charge of metal) to create this doubling effect. We began our studies by testing levels of 15 mM $NO_2$+1/–1 mM EDTA, then further added in 1 uM of $Fe^{2+}$ or 1 uM $Fe^{3+}$. This work indicates that $Fe^{3+}$ is able to recreate this effect when added to the combination, while $Fe^{2+}$ is not, suggesting that a trivalent metal may be necessary. This effect is most likely due to trivalent metals, based on previous papers using Ruthenium, while the most biologically relevant is iron (III).

Other divalent metals ($Mg^{2+}$ and $Ca^{2+}$) were added to the combination to determine if $Fe^{2+}$ is unique or if this a trend. Other biologically relevant trivalent metals (Chromium and Copper) were tested to see if the doubling occurs with them as well. Certain species show greater sensitivity to EDTA/$NO_2^-$ than others, but antagonism is not seen. Azithromycin shows best combination with EDTA/$NO_2^-$ so far. Combination helps reduce the overall thickness of the biofilms.

Initial genetic analysis indicates possible paralysis of NO response. Important metals for PA sensitivity seem to be $Mg^{2+}$ and $Ca^{2+}$, divalent cations known to be associated with LPS of gram negatives. Combination testing in Urine/Artificial Urine suggests that it is effective, but at a lower pH. Cell toxicity studies suggest that cells can survive at the concentrations tested. NO analysis in abiotic systems suggest that the combination produces about twice as much NO as compared to $NO_2$ alone, and this may be due, in part, to Fe(III).

I claim:

1. A composition comprising a therapeutically effective amount of acidified nitrite (A-$NO_2^-$), an iron chelator agent and an antibiotic agent, wherein the iron chelator agent is EDTA or DPTA.

2. The composition of claim 1, wherein the acidified nitrite (A-$NO_2^-$), an iron chelator agent (C), and an antibiotic agent (Ab) are present in a ratio (A-$NO_2^-$:C:Ab) of about 10-600:1-100:0.01-6000.

3. The composition of claim 1, wherein the therapeutically effective amount of A-$NO_2^-$ is between about 5 and about 300 mM.

4. The composition of claim 1, wherein the antibiotic is selected from aminoglycosides, tetracyclines, sulfonamides, fluoroquinolones, macrolides, oxazolidinones, monobactams, cephalosporins, penicillins, polymyxins, glycylcyclines, lincosamides, and combinations thereof.

5. The composition of claim 1, wherein the antibiotic is an aminoglycoside antibiotic.

6. The composition of claim 5, wherein the aminoglycoside antibiotic is tobramycin.

7. The composition of claim 1, wherein the composition is formulated for a mode of administration selected from aerosol, topical, oral, nasal, intravenous, intracranial, intraperitoneal, subcutaneous, intravesicular or intramuscular administration.

8. A method of treating a bacterial infection or colonization comprising administering to a subject in need thereof a composition of claim 1 comprising therapeutically effective amounts of: A-NO2$^-$; an iron chelator; and an antibiotic, resulting in treatment of the bacterial infection or colonization
wherein the iron chelator agent is ETA or DPTA.

9. The method of claim 8, wherein, the acidified nitrite (A-NO$_2^-$), an iron chelator agent (C), and an antibiotic agent (Ab) are present in a ratio (A-NO$_2^-$:C:Ab) of about 10-600:1-100:0.01-6000.

10. The method of claim 8, wherein the therapeutically effective amount of A-NO$_2^-$ is between about 5 and about 300 mM.

11. The method of claim 8, wherein the antibiotic is selected from aminoglycosides, tetracyclines, sulfonamides, fluoroquinolones, macrolides, oxazolidinones, monobactams, cephalosporins, penicillins, polymyxins, glycylcyclines, and lincosamides.

12. The method of claim 8, wherein the antibiotic is an aminoglycoside antibiotic.

13. The method of claim 8, wherein the aminoglycoside antibiotic is tobramycin.

14. The method of claim 8, wherein the bacterial infection is a *P. aeruginosa* infection.

15. The method of claim 8, wherein, the bacterial infection is a lung infection, an ocular infection, a burn infection, a wound infection, a skin infection, a blood infection, a bone infection, a urinary tract infection or a combination of two or more of said infections.

16. The method of claim 8, wherein the composition is formulated for a mode of administration selected from aerosol, topical, oral, nasal, intravenous, intracranial, intraperitoneal, subcutaneous, intravesicular or intramuscular administration.

17. The composition of claim 5, wherein the aminoglycoside antibiotic is azithromycin.

* * * * *

UNITED STATES PATENT AND TRADEMARK OFFICE
CERTIFICATE OF CORRECTION

PATENT NO. : 9,925,206 B2
APPLICATION NO. : 15/066557
DATED : March 27, 2018
INVENTOR(S) : Daniel J. Hassett Page 1 of 1

It is certified that error appears in the above-identified patent and that said Letters Patent is hereby corrected as shown below:

In the Claims

In Column 31, Line 14, the last line of Claim 8 should read:
---- wherein the iron chelator agent is EDTA or DPTA.

Signed and Sealed this
Twenty-eighth Day of August, 2018

Andrei Iancu
*Director of the United States Patent and Trademark Office*